United States Patent
Yates et al.

(10) Patent No.: US 10,478,258 B2
(45) Date of Patent: Nov. 19, 2019

(54) METHODS, SYSTEMS, AND DEVICES FOR CONTROLLING A MOTOR OF A ROBOTIC SURGICAL SYSTEM

(71) Applicant: Ethicon LLC, Guaynabo, PR (US)

(72) Inventors: David C. Yates, West Chester, OH (US); Frederick E. Shelton, IV, Hillsboro, OH (US); Mark Overmyer, Cincinnati, OH (US); Jason L. Harris, Lebanon, OH (US); Jeffrey S. Swayze, Hamilton, OH (US)

(73) Assignee: Ethicon LLC, Guaynabo, PR (US)

( * ) Notice: Subject to any disclaimer, the term of this patent is extended or adjusted under 35 U.S.C. 154(b) by 0 days.

(21) Appl. No.: 15/949,276

(22) Filed: Apr. 10, 2018

(65) Prior Publication Data
US 2018/0221099 A1    Aug. 9, 2018

Related U.S. Application Data

(63) Continuation of application No. 15/237,653, filed on Aug. 16, 2016, now Pat. No. 10,016,246.

(51) Int. Cl.
| | |
|---|---|
| B25J 9/18 | (2006.01) |
| A61B 34/30 | (2016.01) |
| A61B 90/00 | (2016.01) |
| B25J 9/12 | (2006.01) |
| B25J 9/16 | (2006.01) |
| A61B 34/35 | (2016.01) |
| H02K 21/04 | (2006.01) |
| A61B 17/00 | (2006.01) |

(52) U.S. Cl.
CPC .............. *A61B 34/30* (2016.02); *A61B 34/35* (2016.02); *A61B 90/03* (2016.02); *B25J 9/12* (2013.01); *B25J 9/1633* (2013.01); *B25J 9/1689* (2013.01); *H02K 21/04* (2013.01); *A61B 2017/00477* (2013.01); *A61B 2034/302* (2016.02); *A61B 2090/031* (2016.02)

(58) Field of Classification Search
CPC ....................................................... H02P 5/74
See application file for complete search history.

(56) References Cited

U.S. PATENT DOCUMENTS

| | | |
|---|---|---|
| RE30,356 E | 8/1980 | Berman et al. |
| 4,317,072 A | 2/1982 | Goof et al. |
| 4,492,888 A | 1/1985 | Peachee et al. |
| 4,733,118 A | 3/1988 | Mihalko |
| 4,937,485 A | 6/1990 | Mihalko |
| 5,455,473 A | 10/1995 | Lipo et al. |
| 5,672,925 A | 9/1997 | Lipo et al. |
| 5,780,949 A | 7/1998 | Li |
| 5,811,905 A | 9/1998 | Tang |
| 5,825,113 A | 10/1998 | Lipo et al. |

(Continued)

OTHER PUBLICATIONS

Correlated Solutions, "Principle of Digital Image Correlation," 2013 (http://correlatedsolutions.com/digital-image-correlation/).

(Continued)

*Primary Examiner* — Karen Masih
(74) *Attorney, Agent, or Firm* — Mintz Levin Cohn Ferris Glovsky and Popeo, P.C.

(57) ABSTRACT

Various exemplary methods, systems, and devices for controlling a motor of a robotic surgical system are provided.

20 Claims, 19 Drawing Sheets

(56) References Cited

U.S. PATENT DOCUMENTS

| | | |
|---|---|---|
| 5,929,590 A | 7/1999 | Tang |
| 6,008,561 A | 12/1999 | Tang |
| 6,017,354 A | 1/2000 | Culp et al. |
| 6,472,789 B1 | 10/2002 | Akemakou |
| 7,486,043 B2 | 2/2009 | Atarashi |
| 7,538,510 B2 | 5/2009 | Atarashi et al. |
| 7,548,038 B2 | 6/2009 | Atarashi et al. |
| 7,583,048 B2 | 9/2009 | Atarashi et al. |
| 7,615,948 B2 | 11/2009 | Atarashi et al. |
| 7,622,883 B2 | 11/2009 | Kaizuka et al. |
| 7,683,514 B2 | 3/2010 | Onuma et al. |
| 7,772,736 B2 | 8/2010 | Takahashi et al. |
| 8,049,389 B2 | 11/2011 | Abe et al. |
| 8,114,345 B2 | 2/2012 | Dlugos, Jr. et al. |
| 8,224,484 B2 | 7/2012 | Swarup et al. |
| 8,288,982 B2 | 10/2012 | Kauppi |
| 8,373,325 B2 | 2/2013 | Ichiyama |
| 8,390,232 B2 | 3/2013 | Kauppi |
| 8,575,807 B2 | 11/2013 | Merwerth et al. |
| 8,714,948 B2 | 5/2014 | Baba et al. |
| 8,786,233 B2 | 7/2014 | Fair et al. |
| 8,882,792 B2 | 11/2014 | Dietz et al. |
| 8,915,842 B2 | 12/2014 | Weisenburgh, II et al. |
| 8,931,682 B2 | 1/2015 | Timm et al. |
| 8,945,098 B2 | 2/2015 | Seibold et al. |
| 2002/0185929 A1 | 12/2002 | Jang et al. |
| 2005/0057207 A1 | 3/2005 | Bosch et al. |
| 2007/0222404 A1 | 9/2007 | Atarashi |
| 2007/0222405 A1 | 9/2007 | Atarashi et al. |
| 2007/0222406 A1 | 9/2007 | Atarashi et al. |
| 2007/0284961 A1 | 12/2007 | Takahashi et al. |
| 2007/0290633 A1 | 12/2007 | Atarashi et al. |
| 2008/0024082 A1 | 1/2008 | Atarashi et al. |
| 2008/0036415 A1 | 2/2008 | Kaizuka et al. |
| 2008/0081948 A1 | 4/2008 | Weisenburgh et al. |
| 2009/0074594 A1 | 3/2009 | Strasser |
| 2009/0079284 A1 | 3/2009 | Onuma et al. |
| 2009/0096314 A1 | 4/2009 | Atarashi et al. |
| 2009/0100831 A1* | 4/2009 | Sakamoto .............. B60K 17/10 60/492 |
| 2009/0160271 A1 | 6/2009 | Bischof et al. |
| 2009/0267553 A1 | 10/2009 | Labbe et al. |
| 2009/0295245 A1 | 12/2009 | Abe et al. |
| 2009/0315421 A1 | 12/2009 | Onuma et al. |
| 2011/0084567 A1 | 4/2011 | Ichiyama |
| 2011/0118709 A1 | 5/2011 | Burbank |
| 2011/0118778 A1 | 5/2011 | Burbank |
| 2012/0104880 A1 | 5/2012 | Takemoto et al. |
| 2012/0126740 A1 | 5/2012 | Kauppi |
| 2012/0267977 A1 | 10/2012 | Merwerth et al. |
| 2012/0274253 A1 | 11/2012 | Fair et al. |
| 2012/0286615 A1 | 11/2012 | Kauppi |
| 2013/0015727 A1 | 1/2013 | Iki |
| 2013/0107386 A1* | 5/2013 | Sobecki ................. B60R 1/074 359/877 |
| 2013/0154397 A1 | 6/2013 | Sullivan |
| 2013/0158756 A1* | 6/2013 | Yamazaki ............. B60W 20/19 701/22 |
| 2013/0282052 A1 | 10/2013 | Aranyi et al. |
| 2013/0307365 A1 | 11/2013 | Sekiya et al. |
| 2014/0005718 A1 | 1/2014 | Shelton, IV et al. |
| 2014/0327382 A1 | 11/2014 | Fair et al. |
| 2016/0218579 A1 | 7/2016 | Peng et al. |
| 2017/0172672 A1* | 6/2017 | Bailey .................... A61B 34/30 |

OTHER PUBLICATIONS

U.S. Appl. No. 15/131,963 entitled "Method for Operating a Surgical Instrument", filed Apr. 18, 2016.
U.S. Appl. No. 15/177,430 entitled "Surgical Instrument With User Adaptable Techniques", filed Jun. 9, 2016.

* cited by examiner

METHODS, SYSTEMS, AND DEVICES FOR CONTROLLING A MOTOR OF A ROBOTIC SURGICAL SYSTEM

CROSS-REFERENCE TO RELATED APPLICATIONS

The present application claims priority to U.S. patent application Ser. No. 15/237,653 entitled "Methods, Systems, And Devices For Controlling A Motor Of A Robotic Surgical System" filed Aug. 16, 2016, which is hereby incorporated by reference in its entirety.

FIELD

Methods and devices are provided for robotic surgery, and in particular for methods, systems, and devices for controlling a motor of a robotic surgical system.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity, and sensitivity of endoscopic tools has been found to be an impediment in the increased the use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

While significant advances have been made in the field of robotic surgery, there remains a need for improved methods, systems, and devices for use in robotic surgery.

SUMMARY

In general, methods, systems, and devices for controlling a motor of a robotic surgical system are provided.

In one aspect, a surgical device is provided that in one embodiment includes a motor of a robotic surgical system. The motor is configured to drive a function of a surgical tool coupled to the robotic surgical system. The motor includes a plurality of permanent magnets configured to create a permanent magnetic field. A strength of the permanent magnetic field is configured to be selectively electromagnetically reinforced and dampened and thereby create a flattened aspect to a torque speed curve of the motor to enable a shiftable speed ratio.

The surgical device can have any number of variations. For example, the motor can include a second plurality of magnets configured to create a second magnetic field, and the second magnetic field can be configured to selectively electromagnetically reinforce and dampen the strength of the permanent magnetic field. In at least some embodiments, the plurality of permanent magnets can be arranged radially around the second plurality of magnets. In at least some embodiments, each of the second plurality of magnets can include an iron member and a rare earth magnet operatively coupled to the iron member. Each of the iron members can be an iron sleeve disposed around the rare earth magnet operatively coupled thereto such that the motor includes a plurality of paired iron sleeves and rare earth magnets, and, in at least some embodiments, each of the paired iron sleeves and rare earth magnets can have a wire coiled therearound. Each of the iron members can be an iron bar separate from and in operative distance of the rare earth magnet operatively coupled thereto, and, in at least some embodiments, each of the iron bars can have a wire coiled therearound, and none of the wires can be coiled around the rare earth magnets.

For another example, the flattened aspect can allow the motor to apply a single predictable torque. In at least some embodiments, the flattened aspect to the torque speed curve can extend between a first speed of the motor and a second, higher speed of the motor that define the shiftable speed ratio.

For yet another example, the motor can be configured to receive a voltage input thereto, and different amounts of the voltage input can cause the selective electromagnetic reinforcing and dampening.

In another embodiment, a surgical device is provided that includes a motor of a robotic surgical system. The motor is configured to drive a function of a surgical tool coupled to the robotic surgical system. The motor has a first electromagnetic field and a second electromagnetic field that interacts with the first electromagnetic field. The second electromagnetic field is configured to be selectively adjusted between a first strength corresponding to a first speed of the motor and a second, higher strength corresponding to a second, higher speed of the motor. The motor is configured to deliver a substantially same force to the surgical tool to drive the function when the motor has either the first speed or the second speed.

The surgical device can vary in any number of ways. For example, the motor can be configured to deliver a variable force to the surgical tool to drive the function when the motor has a speed less than the first speed or greater than the second speed. For another example, the second speed can be about twice the first speed.

For yet another example, the motor can include a first plurality of magnets that contribute to the first electromagnetic field and a second plurality of magnets that contribute to the second electromagnetic field, and each of the first plurality of magnets can be a permanent magnet. In at least some embodiments, the first plurality of permanent magnets can be arranged radially around the second plurality of magnets, and/or each of the second plurality of magnets can include an iron member and a rare earth magnet operatively coupled to the iron member.

In another embodiment, a surgical device is provided that includes a motor of a robotic surgical system configured to removably and replaceably couple to a surgical tool. The motor is configured to deliver a torque to the surgical tool removably and replaceably coupled to the robotic surgical system, and the motor includes a wire winding that generates a current configured to prevent a speed of the motor from exceeding a predetermined threshold amount of speed and thereby limit an amount of the delivered torque.

The surgical device can vary in any number of ways. For example, the motor can include a switch, and the current generated by the wire winding exceeding a predetermined threshold amount of current can be configured to open the switch and thereby prevent the speed of the motor from exceeding the predetermined threshold amount of speed and thereby limit the amount of the delivered torque. In at least some embodiments, the motor can be configured to generate an electromagnetic field, and the opening of the switch can be configured to reduce a strength of the electromagnetic field and thereby reduce the speed of the motor. In at least some embodiments, a number of times the wire is wound can define the predetermined threshold amount of current.

For another example, the wire can be wound around a shaft of the motor. In at least some embodiments, rotation of the shaft can be configured to generate the current.

In another embodiment, a surgical device is provided that includes a motor of a robotic surgical system configured to removably and replaceably couple to a surgical tool. The motor is configured to deliver a torque to the surgical tool removably and replaceably coupled to the robotic surgical system. The motor is configured to generate an electromagnetic field, and the motor is configured to self-reduce the electromagnetic field to prevent the delivered torque from exceeding a predetermined threshold amount of torque.

The surgical device can have any number of variations. For example, the motor can include a plurality of wires each wound around a different set of magnets, all of the magnets can be configured to contribute to generation of the electromagnetic field, and the motor self-reducing the electromagnetic field can include the motor stopping one of the sets of magnets from contributing to the generation of the electromagnetic field.

For another example, the motor can include a shaft having a wire wound therearound, rotation of the shaft can be configured to generate a current, and the current exceeding a predetermined amount of current can cause the motor to reduce the electromagnetic field. In at least some embodiments, the motor can include a plurality of wires each wound around a different set of magnets, all of the magnets can be configured to contribute to generation of the electromagnetic field, and the current exceeding the predetermined amount of current can cause the motor to stop one of the sets of magnets from contributing to the generation of the electromagnetic field and thereby reduce the electromagnetic field. In at least some embodiments, the motor can include a switch operatively coupled to the one of the sets of magnets, and the current exceeding the predetermined amount of current can cause the motor to open the switch.

For still another example, a speed of the motor can correlate to an amount of the delivered torque, and the motor being configured to self-reduce the electromagnetic field can include the motor reducing the speed of the motor.

In another aspect, a surgical method is provided that in one embodiment includes using a robotic surgical system to advance a working end of a surgical tool into a body of a patient. The robotic surgical system includes a motor having a first electromagnetic field and a second electromagnetic field that interacts with the first electromagnetic field. The surgical method also includes adjusting a strength of the second electromagnetic field to cause a motor of the robotic surgical system to have a first speed and thereby deliver a first torque to the surgical tool to cause the working end of the surgical tool to perform a first function in the body of the patient, and adjusting the strength of the second electromagnetic field to cause the motor to have a second speed and thereby deliver a second torque to the surgical tool to cause the working end of the surgical tool to perform a second function in the body of the patient. The first speed is greater than the first speed, and the first torque and the second torque are substantially equal.

The surgical method can vary in any number of ways. For example, the motor can include a plurality of permanent magnets that contribute to the first electromagnetic field, and the motor can include a second plurality of magnets that contribute to the second electromagnetic field and that each include an iron member and a rare earth magnet operatively coupled to the iron member. For another example, the second speed can be about twice the first speed.

In another embodiment, a surgical method is provided that includes receiving at a surgical tool a torque from a robotic surgical system to drive a function of the surgical tool. The surgical tool is removably and replaceably coupled to the robotic surgical system. The surgical method also includes generating a current at the surgical tool in response to the receipt of the torque, and transmitting the generated current from the surgical tool to the robotic surgical system and thereby prevent the torque received at the surgical tool from exceeding a predetermined maximum amount of torque.

The surgical method can vary in any number of ways. For example, the torque received at the surgical tool can cause an elongate shaft of the surgical tool to rotate, and a speed of the rotation of the shaft can define an amount of the generated current. For another example, the robotic surgical system can include a motor, and the generated current exceeding a predetermined threshold amount of current can cause the motor to slow down and thereby prevent the torque received at the surgical tool from exceeding the predetermined maximum amount of torque. For yet another example, the robotic surgical system can include a motor, and the generated current can cause a change in a strength of an electromagnetic field generated by the motor and thereby prevent the torque received at the surgical tool from exceeding the predetermined maximum amount of torque.

For still another example, the surgical method can include receiving at a second surgical tool a second torque from the robotic surgical system to drive a function of the second surgical tool. The second surgical tool is removably and replaceably coupled to the robotic surgical system. The surgical method also includes generating a second current at the second surgical tool in response to the receipt of the second torque, and transmitting the generated second current from the second surgical tool to the robotic surgical system and thereby prevent the second torque received at the second surgical tool from exceeding a second predetermined maximum amount of torque that is different from the predetermined maximum amount of torque.

In another embodiment, a surgical method is provided that includes actuating a motor of a robotic surgical system to cause the motor rotate at a speed and thereby provide a torque to a surgical tool removably and replaceably coupled to the robotic surgical system to drive a function of the surgical tool. The surgical method also includes generating a current at the motor in response to the actuating of the motor, and reducing the speed of the motor in response to the generated current exceeding a predetermined threshold amount of current and thereby reducing the torque provided to the surgical tool.

The surgical method can have any number of variations. For example, the motor can include a switch, and reducing the speed of the motor can include opening the switch. For another example, the motor can include a shaft having a wire wound therearound, the actuation of the motor can cause the shaft to rotate, and the rotation of the shaft can generate the current.

For yet another example, the actuation of the motor can cause generation of an electromagnetic field at the motor, and reducing the speed of the motor can include reducing a strength of the electromagnetic field. In at least some embodiments, the motor can include a plurality of wires each wound around a different set of magnets, all of the magnets can be configured to contribute to the generation of the electromagnetic field, and reducing the strength of the electromagnetic field can include stopping one of the sets of magnets from contributing to the generation of the electromagnetic field. In at least some embodiments, the motor can include a switch operatively coupled to the one of the sets of magnets, and opening the switch can stop the one of the sets of magnets from contributing to the generation of the electromagnetic field.

In another aspect, a surgical system is provided that in one embodiment includes a surgical tool having a housing configured to removably and replaceably couple to a robotic surgical system, an elongate shaft extending distally from the housing, an end effector at a distal end of the shaft configured to perform a function in a body of a patient. The surgical tool is configured to receive a torque from the robotic surgical system when removably and replaceably coupled to the robotic surgical system. The surgical tool is configured to limit a maximum torque delivered from the robotic surgical system to the surgical tool by sensing at least one of a current applied by the robotic surgical system to the surgical tool and a speed of rotation of the shaft.

The surgical system can vary in any number of ways. For example, the surgical tool can be configured to sense at least the current applied by the robotic surgical system to the surgical tool, and the surgical tool can be configured to limit the maximum torque in response to the sensed current exceeding a predetermined threshold current. For another example, the surgical tool can be configured to sense at least the speed of rotation of the shaft, and the surgical tool can be configured to limit the maximum torque in response to the sensed speed of rotation exceeding a predetermined threshold speed of rotation.

For yet another example, the surgical system can include a motor of the robotic surgical system. In at least some embodiments, the motor can be configured to drive the torque, and the sensed at least one of the current applied by the robotic surgical system to the surgical tool and the speed of rotation of the shaft exceeding a predetermined threshold can cause the motor to slow down and thereby limit the maximum torque. In at least some embodiments, the motor can be configured to drive the torque, the motor can include first and second wire windings around first and second magnets that contribute to generation of an electromagnetic field, and the sensed at least one of the current applied by the robotic surgical system to the surgical tool and the speed of rotation of the shaft exceeding a predetermined threshold can cause one of the first and second wire windings to no longer contribute to the generation of the electromagnetic field and thereby limit the maximum torque.

For still another example, the surgical tool can be configured to generate a current in response to receipt of the torque from the robotic surgical system, and the surgical tool can be configured to deliver the generated current to the robotic surgical system to limit the maximum torque. In at least some embodiments, the shaft can have a wire wound therearound that is configured to generate the current in response to the shaft rotating. A number of times the wire is wound around the shaft can define a threshold value of the generated current that causes the maximum applicable torque to be limited. In at least some embodiments, the surgical system can include a motor of the robotic surgical system, the motor can be configured to drive the torque, and the generated current delivered to the robotic surgical system can be configured to cause the motor to provide less torque to the surgical tool. In at least some embodiments, the surgical system can include a switch of the robotic surgical system that can be operatively coupled to the motor, and the generated current delivered to the robotic surgical system exceeding a predetermined threshold current can be configured to actuate the switch and thereby cause the motor to provide less torque to the surgical tool. In at least some embodiments, the motor can have first and second wire windings around first and second magnets that contribute to generation of an electromagnetic field, and the generated current delivered to the robotic surgical system exceeding a predetermined threshold current can be configured to cause one of the first and second wire windings to no longer contribute to the generation of the electromagnetic field and thereby limit the maximum applicable torque.

In another embodiment, a surgical system is provided that includes a surgical tool configured to removably and replaceably couple to a robotic surgical system. The surgical tool is configured to receive a torque from the robotic surgical system when removably and replaceably coupled thereto to drive a function of the surgical tool. The surgical tool is configured to transmit an electrical signal to the robotic surgical system removably and replaceably coupled thereto. The electrical signal is configured to prevent the robotic surgical system from providing an amount of the torque to the surgical tool that exceeds a predetermined threshold amount of torque.

The surgical system can have any number of variations. For example, the surgical tool can be configured to generate a current in response to the received torque, and the electrical signal can reflect the generated current exceeding a predetermined threshold amount of current. For another example, the surgical system can include a motor of the robotic surgical system, the motor can be configured to drive the torque, and the electrical signal can be configured to reduce a speed of the motor and thereby prevent the robotic surgical system from providing the amount of torque to the surgical tool that exceeds the predetermined threshold amount of torque.

For yet another example, the surgical system can include a second surgical tool configured to removably and replaceably couple to the robotic surgical system. The second surgical tool can be configured to receive a second torque from the robotic surgical system when removably and replaceably coupled thereto to drive a function of the second surgical tool. The second surgical tool can be configured to transmit a second electrical signal to the robotic surgical system removably and replaceably coupled thereto. The second electrical signal can be configured to prevent the robotic surgical system from providing an amount of torque to the second surgical tool that exceeds a second predetermined threshold amount of torque that is different from the first predetermined threshold amount of torque.

BRIEF DESCRIPTION OF DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods, systems, and devices for controlling a motor of a robotic surgical system are provided.

Robotic Surgical Systems

The systems, devices, and methods disclosed herein can be implemented using a robotic surgical system.

As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication.

Figure 1:
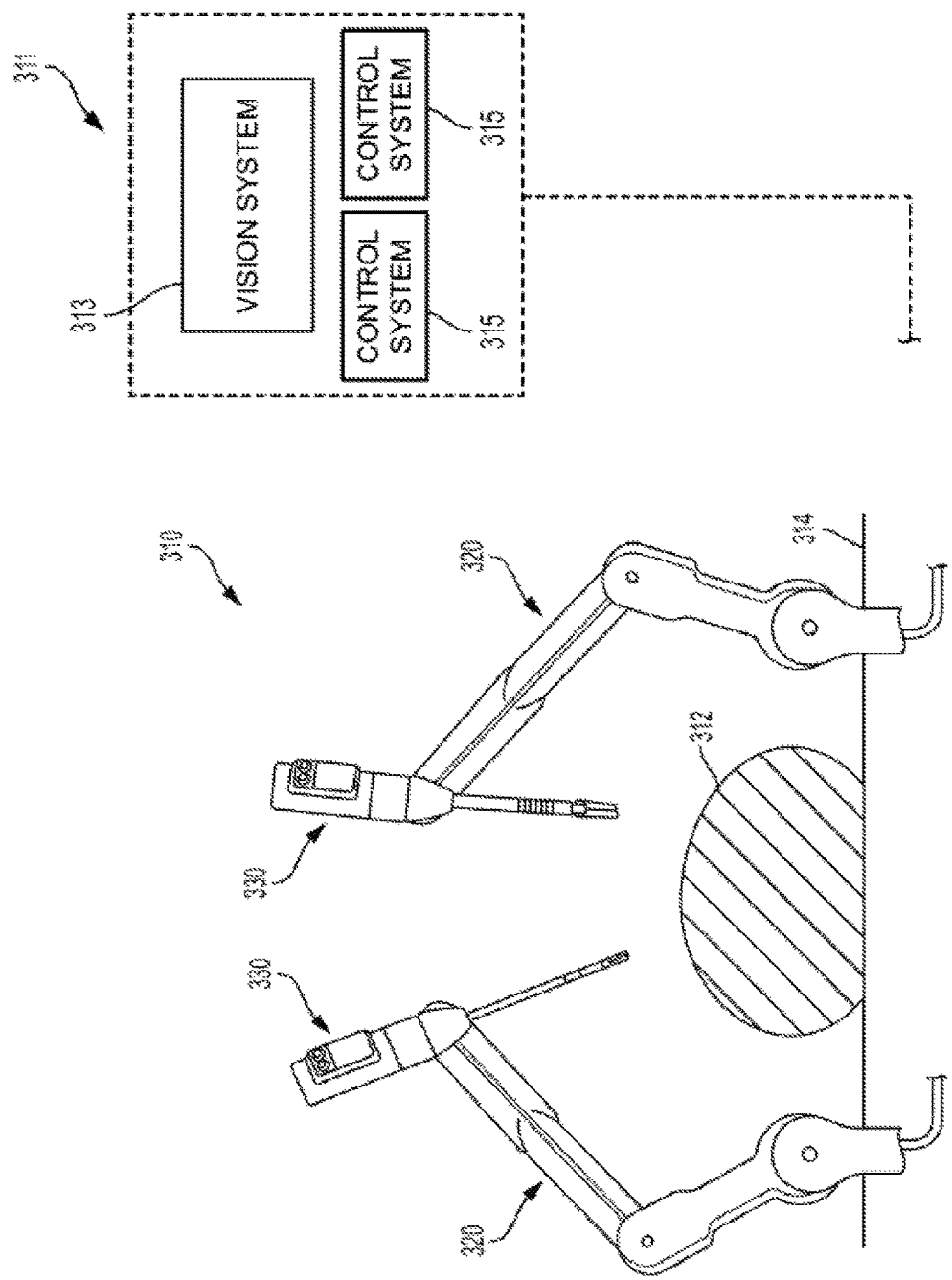
FIG. 1 is a perspective view of one embodiment of a surgical robotic system that includes a patient-side portion and a user-side portion.

FIG. 1 is a perspective view of one embodiment of a surgical robotic system 300 that includes a patient-side portion 310 that is positioned adjacent to a patient 312, and a user-side portion 311 that is located a distance from the patient, either in the same room and/or in a remote location. The patient-side portion 310 generally includes one or more robotic arms 320 and one or more tool assemblies 330 that are configured to releasably couple to a robotic arm 320. The user-side portion 311 generally includes a vision system 313 for viewing the patient 312 and/or surgical site, and a control system 315 for controlling the movement of the robotic arms 320 and each tool assembly 330 during a surgical procedure.

The control system 315 can have a variety of configurations and can be located adjacent to the patient, e.g., in the operating room, remote from the patient, e.g., in a separate control room, or the control system 315 can be distributed at two or more locations. For example, a dedicated system control console can be located in the operating room, and a separate console can be located in a remote location. The control system 315 can include components that enable a user to view a surgical site of a patient 312 being operated on by the patient-side portion 310 and/or to control one or more parts of the patient-side portion 310 (e.g., to perform a surgical procedure at the surgical site 312). In some embodiments, the control system 315 can also include one or more manually-operated input devices, such as a joystick, exoskeletal glove, a powered and gravity-compensated manipulator, or the like. These input devices can control teleoperated motors which, in turn, control the movement of the surgical system, including the robotic arms 320 and tool assemblies 330.

The patient-side portion can also have a variety of configurations. As depicted in FIG. 1, the patient-side portion 310 can couple to an operating table 314. However, in some embodiments, the patient-side portion 310 can be mounted to a wall, to the ceiling, to the floor, or to other operating room equipment. Further, while the patient-side portion 310 is shown as including two robotic arms 320, more or fewer robotic arms 320 may be included. Furthermore, the patient-side portion 310 can include separate robotic arms 320 mounted in various positions, such as relative to the surgical table 314 (as shown in FIG. 1). Alternatively, the patient-side portion 310 can include a single assembly that includes one or more robotic arms 320 extending therefrom.

Figure 2:
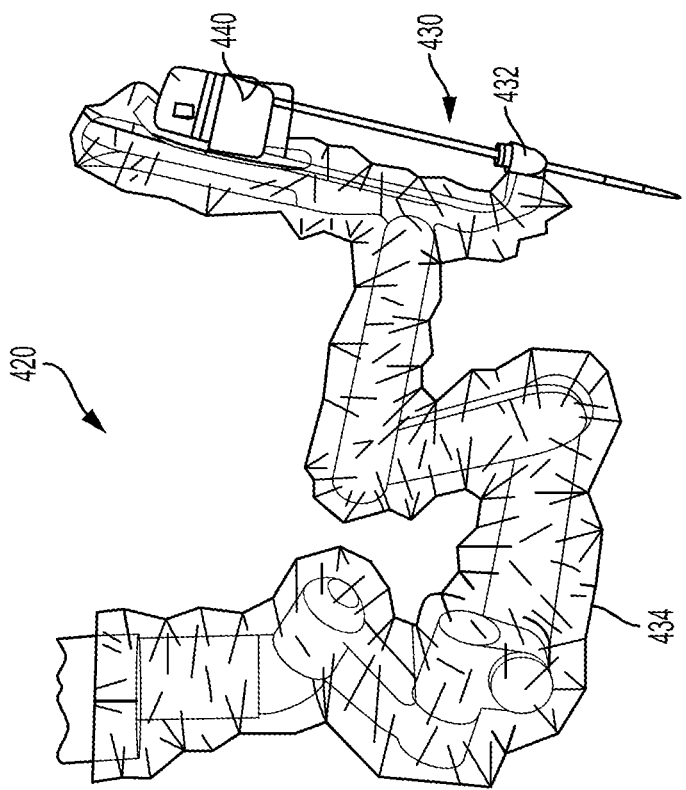
FIG. 2 is a perspective view of one embodiment of a robotic arm of a surgical robotic system with a surgical tool releasably and removably coupled to the robotic arm.

FIG. 2 illustrates one embodiment of a robotic arm 420 and a tool assembly 430 releasably coupled to the robotic arm 420. The robotic arm 420 can support and move the associated tool assembly 430 along one or more mechanical degrees of freedom (e.g., all six Cartesian degrees of freedom, five or fewer Cartesian degrees of freedom, etc.).

The robotic arm 420 can include a tool driver 440 at a distal end of the robotic arm 420, which can assist with controlling features associated with the tool assembly 430. The robotic arm 420 can also include an entry guide 432 (e.g., a cannula mount or cannula) that can be a part of or removably coupled to the robotic arm 420, as shown in FIG. 2. A shaft 436 of the tool assembly 430 can be inserted through the entry guide 430 for insertion into a patient.

In order to provide a sterile operation area while using the surgical system, a barrier 434 can be placed between the actuating portion of the surgical system (e.g., the robotic arm 420) and the surgical instruments (e.g., the tool assembly 430). A sterile component, such as an instrument sterile adapter (ISA), can also be placed at the connecting interface between the tool assembly 430 and the robotic arm 420. The placement of an ISA between the tool assembly 430 and the robotic arm 420 can ensure a sterile coupling point for the tool assembly 430 and the robotic arm 420. This permits removal of tool assemblies 430 from the robotic arm 420 to exchange with other tool assemblies 430 during the course of a surgery without compromising the sterile surgical field.

Figure 3:
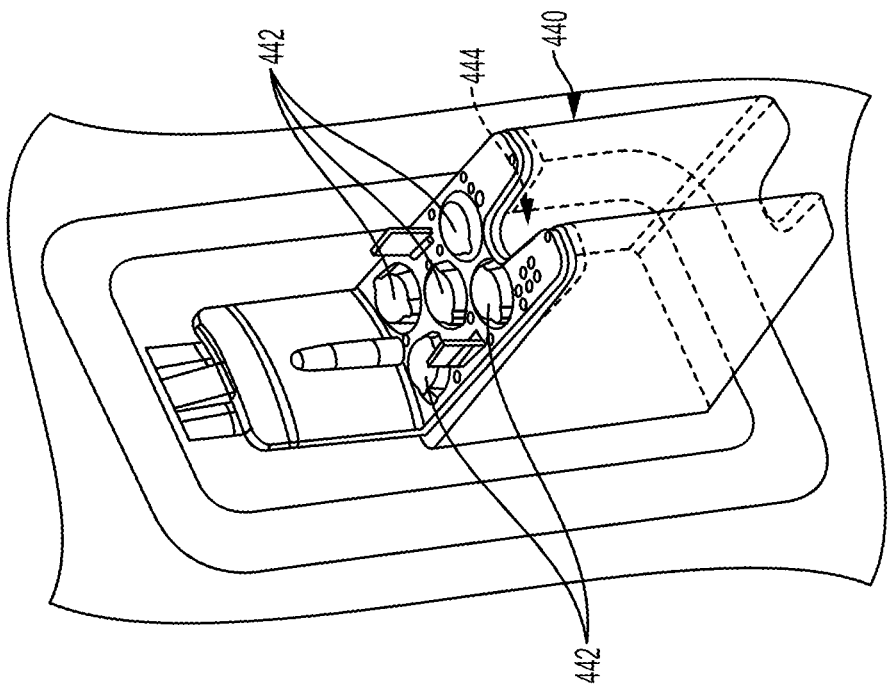
FIG. 3 is a perspective view of a tool driver of the robotic arm of FIG. 2.

FIG. 3 illustrates the tool driver 440 in more detail. As shown, the tool driver 440 includes one or more motors, e.g., five motors 442 are shown, that control a variety of movements and actions associated with the tool assembly 430, as will be described in greater detail below. For example, each motor 442 can couple to and/or interact with an activation feature (e.g., gear) associated with the tool assembly 430 for controlling one or more actions and movements that can be performed by the tool assembly 430, such as for assisting with performing a surgical operation. The motors 442 are accessible on the upper surface of the tool driver 440, and thus the tool assembly is configured to mount on top of the tool driver 440 to couple thereto. The tool driver 440 also includes a shaft-receiving channel 444 formed in a sidewall thereof for receiving the shaft of the tool assembly 430. In other embodiments, the shaft can extend through on opening in the tool driver 440, or the two components can mate in various other configurations.

Figure 4:
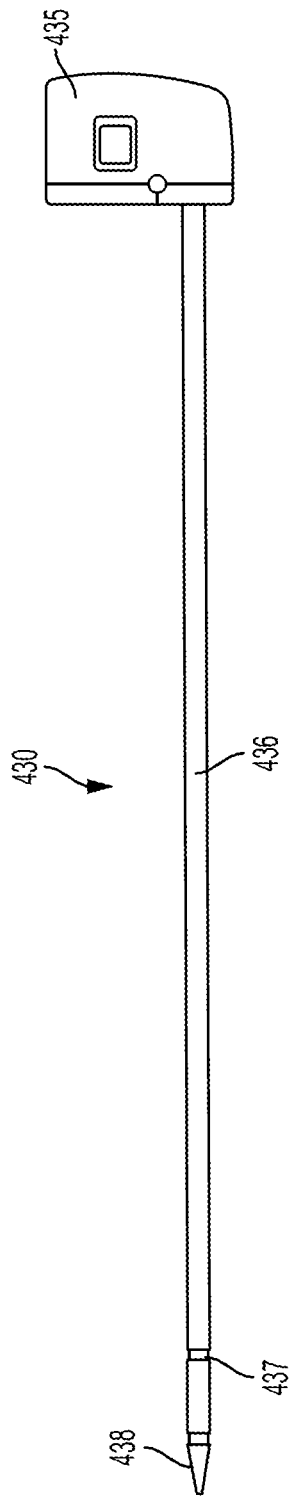
FIG. 4 is a side view of the surgical tool of FIG. 2 uncoupled from the robotic arm, the tool including a shaft extending from a puck at a proximal end and having an end effector located at a distal end of the shaft.

FIG. 4 illustrates the tool assembly 430 uncoupled from the robotic arm 420. The tool assembly 430 includes a housing or puck 435 coupled to a proximal end of the shaft 436 and an end effector 438 coupled to a distal end of the shaft 436. The puck 435 can include coupling features that assist with releasably coupling the puck 435 to the tool driver 440 of the robotic arm 420. The puck 435 can include gears and/or actuators that can be actuated by the one or more motors 442 in the driver 440, as will be described in greater detail below. The gears and/or actuators in the puck 435 can control the operation of various features associated with the end effector 438 (e.g., clamping, firing, rotation, articulation, energy delivery, etc.), as well as control the movement of the shaft 436 (e.g., rotation of the shaft).

The shaft 436 can be fixed to the puck 435, or it can be releasably coupled to the puck 435 such that the shaft 436 can be interchangeable with other shafts. This can allow a single puck 435 to be adaptable to various shafts 436 having different end effectors 438. The shaft 436 can include actuators and connectors that extend along the shaft and assist with controlling the actuation and/or movement of the end effector 438 and/or shaft 436. The shaft 436 can also include one or more joints or wrists 437 that allow a part of the shaft 436 or the end effector 438 to articulate relative to the longitudinal axis of the shaft 436. This can allow for fine movements and various angulation of the end effector 438 relative to the longitudinal axis of the shaft 436. The end effector 438 can include any of a variety of surgical tools, such as a stapler, a clip applier, forceps, a needle driver, a cautery device, a cutting tool, a pair of jaws, an imaging device (e.g., an endoscope or ultrasound probe), or a combined device that includes a combination of two or more various tools.

Figure 5:
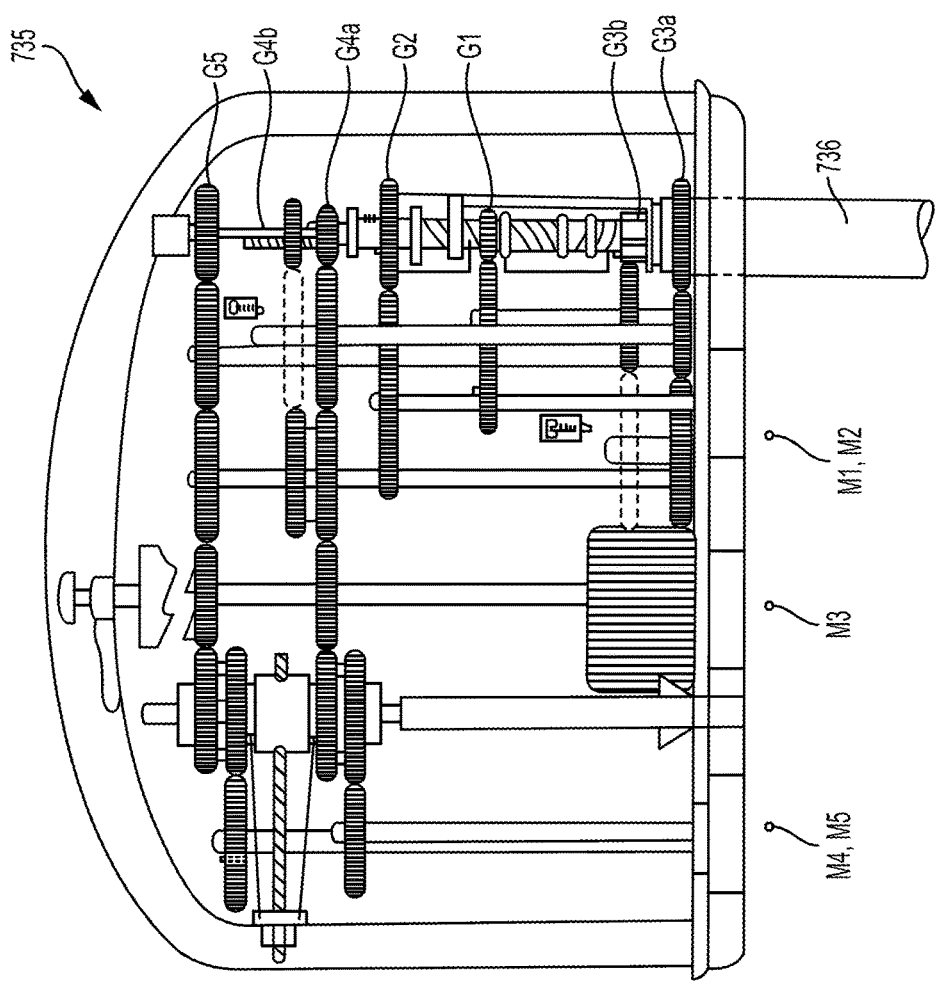
FIG. 5 is a partial cross-sectional side view of another embodiment of a puck and shaft of a surgical tool.

FIG. 5 illustrates an embodiment of a puck 735 and a proximal end of a shaft 736 extending from the puck 735. As shown in FIG. 5, the puck 735 includes a plurality of actuation gears and gear shafts that can be either directly or indirectly controlled by any one of the motors 442 associated with the driver 440. For example, as shown in FIG. 5, the puck 735 is configured to couple to five motors at the locations indicated by reference numbers M1, M2, M3, M4, and M5. In this embodiment, the puck 735 includes first and second articulation gears G1, G2 that are coupled respectively to the first and second motors M1, M2 via a series of one or more additional gears and shafts. Actuation of the first and second motors M1, M2 will rotate the articulation gears G1, G2, which in turn cause linear movement of an articulation cable in a proximal or distal direction to thereby cause articulation of an end effector at a distal end of the shaft 736 in desired left and right directions. The puck 735 also includes a shaft rotation gear G3a that is coupled to the third motor M3 via a series of one or more additional gears and shafts. Actuation of the third motor M3 will thus rotate the shaft rotation gear G3a, thereby causing rotation of the shaft 736. The third motor M3 can also be configured to shift and to couple, via a series of one or more additional gears and shafts, to a head rotation gear G3b, which will cause rotation of the end effector relative to the shaft 736. The puck 735 further includes a firm dose gear G4a that is coupled to the fourth motor M4 via a series of one or more additional gears and shafts. Actuation of the fourth motor M4 will rotate the firm close gear G4a to cause linear translation of a drive screw to firmly close the jaws of the end effector. The puck 735 further includes a quick close gear G4b that can also couple to the fourth motor M4 via a series of one or more additional gears and shafts. When motor M4 is shifted into engagement with the quick close gear G4b, actuation of the fourth motor M4 will rotate the quick close gear G4b to cause linear translation of a quick close cable to quickly close the jaws of the end effector. Finally, the illustrated puck 735 includes a firing gear G5 that is coupled to the fifth motor M5 via a series of one or more additional gears and shafts. Actuation of the fifth motor M5 will rotate the firing gear G5, thereby driving a lead screw linearly to advance a sled through the end effector, as will be discussed in more detail below.

Figure 6:
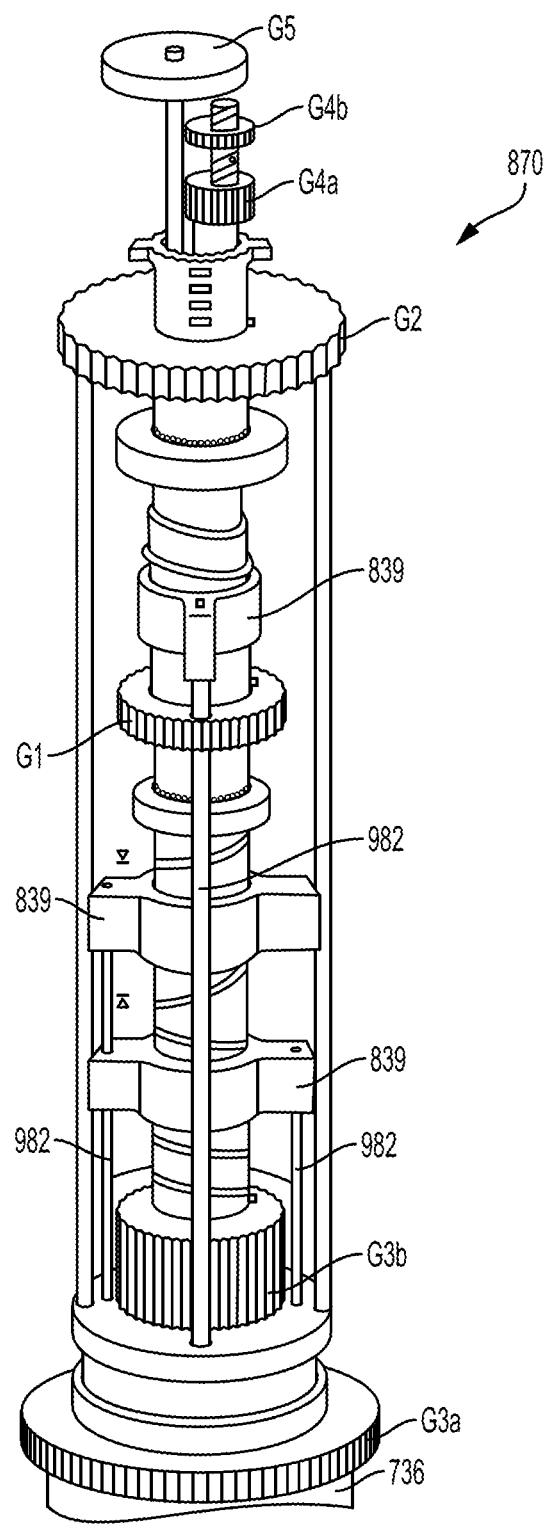
FIG. 6 is a perspective view of an actuation assembly of the puck of FIG. 5.
Figure 7:
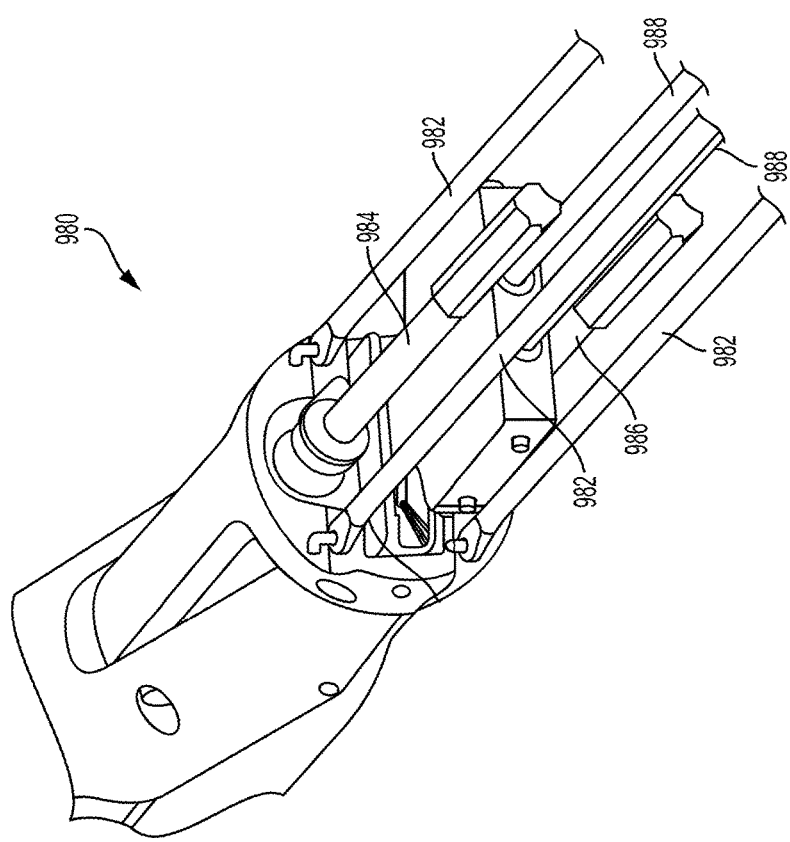
FIG. 7 is a perspective view of a wrist portion of the surgical tool of FIG. 4.

FIG. 6 illustrates actuation assembly 870 components of the puck of FIG. 5. As shown and indicated above, each of the gears G1, G2, G3, G4, G5 is coupled to an actuation shaft that extends from the actuation assembly 870 and along the shaft 736 of the tool assembly, such as for controlling the movements of the end effector. FIG. 7 illustrates a distal end of the actuation shafts extending from a wrist 980 located just proximal of the end effector. The wrist 980 can allow for fine movements and angulation of the end effector relative to the proximal end of the shaft 736. As shown in FIG. 7, the wrist 980 includes four articulation cables 982 that are spaced around a perimeter of the wrist 980. When actuated (e.g., pushed, pulled, rotated), the articulation cables 982 will cause articulation of the end effector (e.g., movement up, down, left, right, and combinations thereof) relative to the proximal end of the shaft 736. The articulation cables 982 are connected to articulation couplers 839, shown in FIG. 6, that are driven proximally and distally when the articulation gears G1, G2 are actuated by the first and second motors M1, M2. The wrist 980 also includes an upper rotary driver 984 that when actuated can cause the pair of jaws of the end effector to firmly close. The upper rotary driver 984 is coupled to the firm close gear G4a shown in FIG. 6 such that rotation of the firm close gear G4a by the motor M4 causes rotation of the rotary driver 984. The wrist 980 can also include a lower rotary driver 986 that when actuated can cause movement of a sled located at the end effector. The lower rotary driver 986 is coupled to the firing gear G5 shown in FIG. 6 and it likewise rotates in response to rotation of the firing gear G5. The illustrated wrist 980 further includes a linear pull cable 988 that is coupled to the quick close gear G4b shown in FIG. 6 and that moves linearly in a proximal direction to cause rapid close of the pair of jaws of the end effector.

Figure 8:
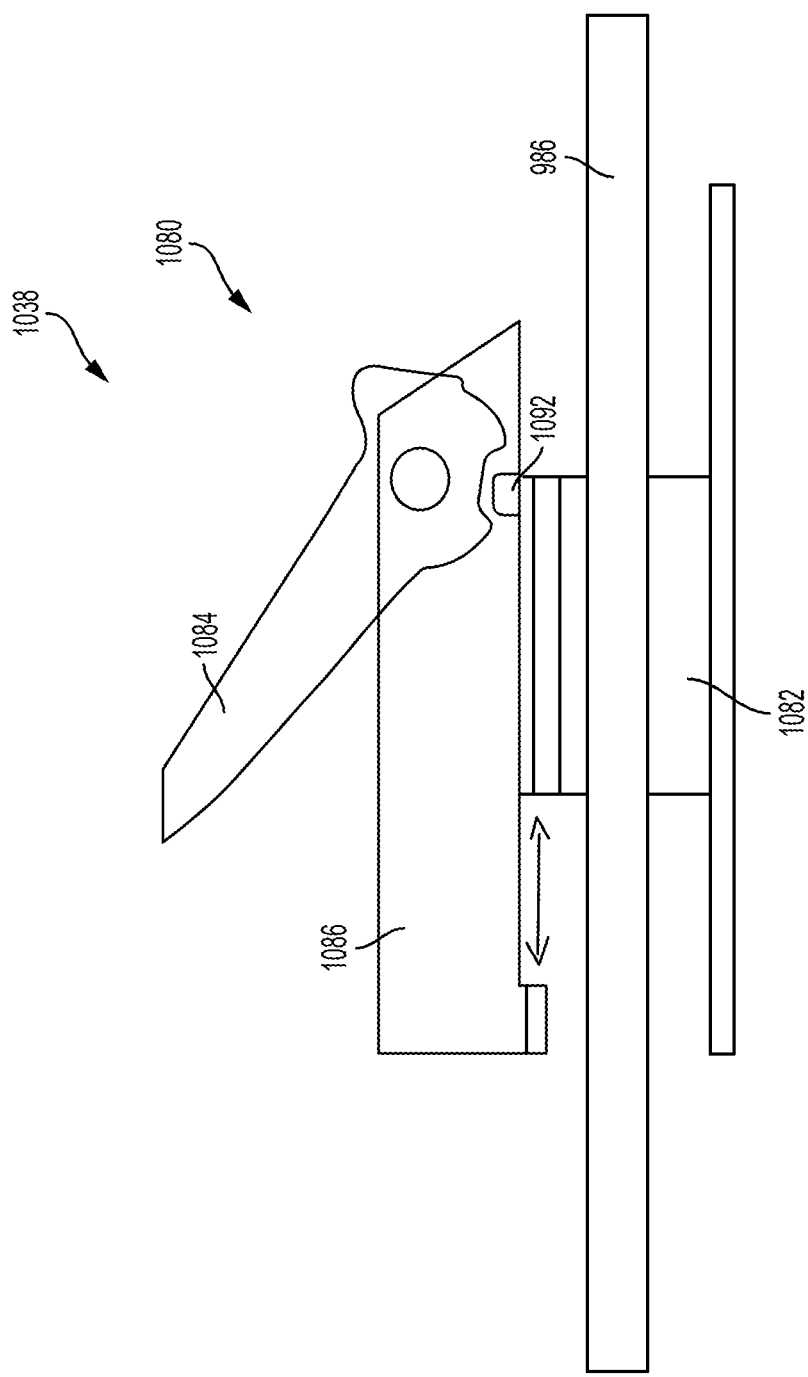
FIG. 8 is a partial side schematic view of one embodiment of an end effector having a knife actuation assembly.

FIG. 8 illustrates a portion of an end effector 1038 having a knife actuation assembly 1080 that includes a drive member 1082, a knife 1084, a knife sled 1086, and a lead screw or rotary driver 986. The drive member 1082 includes internal threads that are threadably coupled with the rotary driver 986. Such coupling can allow drive member 1082 to move along the rotary driver 986 when the rotary driver 986 is rotated. As discussed above, the rotary driver 986 can be actuated at the wrist 980, as shown in FIG. 7, thereby causing rotation of the rotary driver 986 and linear movement of the knife sled 1086 along the rotary driver 986. The rotary driver 986 is coupled to the firing gear G5 shown in FIG. 6. The knife actuation assembly 1080 is configured to orient the knife 1084 in a cutting position when the drive member 1082 pushes the knife sled 1086 along the rotary driver 986 and to stow the knife 1084 when the drive member 1082 is moved proximally relative to the knife sled 1086. In operation, the rotary driver 986 is first rotated to advance the drive member 1082 distally along the rotary driver 986 thereby pushing the knife sled 1086 in the distal direction and angularly orienting the knife 1084 in the cutting position. At the end of the distal movement of the assembly 1080, the direction of rotation of the rotary driver 986 is reversed to retract the drive member 1082 proximally relative to the knife sled 1086, thereby causing the knife 1084 to rotate down into the stowed position, such as via interaction between an interface feature 1092 and the knife 1084.

A motor of a robotic surgical system (e.g., the motors M1, M2, M3, M4, M5 of FIG. 5, a motor of the robotic surgical system 310 of FIG. 1, the motors 442 of the tool driver 440 of FIG. 3, etc.) provides a torque to a surgical tool (e.g., the tool assemblies 330 of FIG. 1, the tool assembly 430 of FIG. 4, etc.) coupled to the robotic surgical system to drive a function of the surgical tool. The motor can include a stepper motor that includes a plurality of magnets configured to generate an electromagnetic field, an element configured to rotate in response to the electromagnetic field, and a shaft operably coupled to the element that rotates in response to the rotation of the central element. The rotating shaft is configured to provide the torque to the surgical tool, e.g., to a puck of the surgical tool coupled to a tool driver that includes the motor.

Functions of the surgical tool can include a function of an end effector of the surgical tool. Functions of the end effector can include, for example, a quick close of the end effector (e.g., closing jaws of the surgical tool at a first speed), a slower close of the end effector (e.g., closing jaws of the surgical tool at a second speed that is less than the first speed associated with quick close), articulation of the end effector relative to an elongate shaft of the surgical tool (e.g., angling the end effector relative to a longitudinal axis of the elongate shaft), rotation of the end effector relative to the elongate shaft (e.g., rotation of the end effector about a longitudinal axis thereof), and rotation of the end effector and the shaft as a unit about the longitudinal axis of the shaft.

In at least some embodiments, the element of the motor can be configured to generate a second electromagnetic field that interacts with the electromagnetic field generated by the plurality of magnets (referred to for clarity of discussion as the "first electromagnetic field") to reinforce or dampen the first electromagnetic field and thereby make the motor stronger or weaker. The motor can thus be configured to selectively provide a stronger torque to the surgical tool or a weaker torque to the surgical tool, which may allow for more efficient use of the motor and/or help prevent more torque than is needed to perform a function from being provided to the surgical tool. In other words, the motor can be shifted between providing a first amount of torque to the surgical tool and providing a second amount of torque to the surgical tool that is greater than the first amount of torque.

Figure 9:
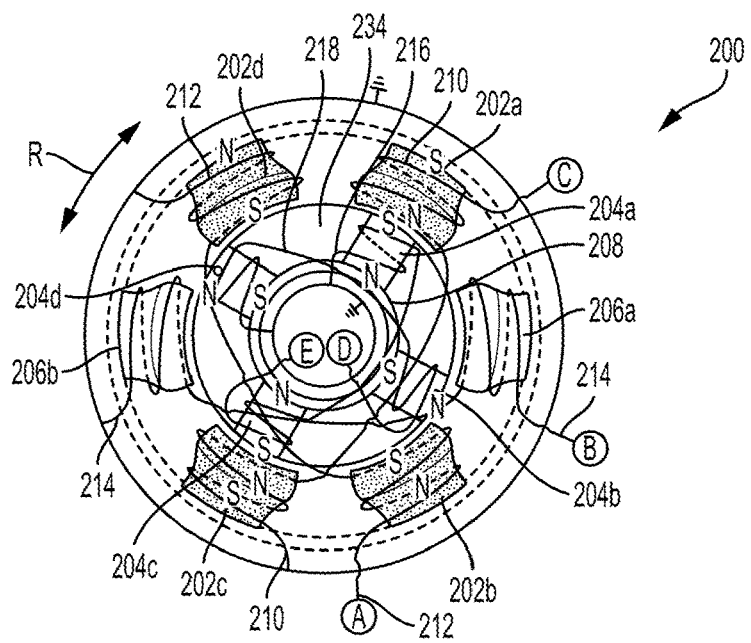
FIG. 9 is a side partially cross-sectional schematic view of one embodiment of a motor.
Figure 10:
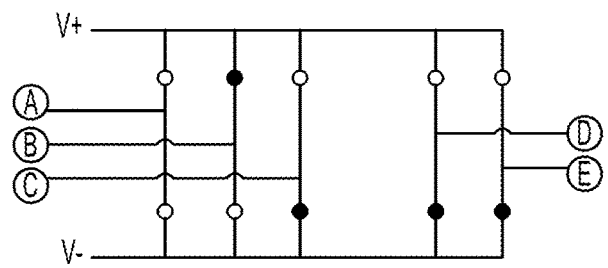
FIG. 10 is a circuit view of the motor of FIG. 9.

FIG. 9 illustrates one embodiment of a motor 200 configured to generate first and second electromagnetic fields. FIG. 10 illustrates a circuit view of the motor 200. The motor 200 includes a first plurality of magnets 202a, 202b, 202c, 202d that contribute to the first electromagnetic field, a second plurality of magnets 204a, 204b, 204c, 204d that contribute to the second electromagnetic field, a third plurality of magnets 206a, 206b that are neutral, and a shaft 208. The first plurality of magnets 202a, 202b, 202c, 202d and the third plurality of magnets 206a, 206b are arranged radially around the second plurality of magnets 204a, 204b, 204c, 204d, which are configured to move relative to the first plurality of magnets 202a, 202b, 202c, 202d and the third plurality of magnets 206a, 206b.

A first wire 210 is coiled around a first pair of the first plurality of magnets 202a, 202c, a second wire 212 is coiled around a second pair of the first plurality of magnets 202b, 202d, and a third wire 214 is coiled around the pair of neutral magnets 206a, 206b. As shown in FIGS. 9 and 10, the first wire 210 coiled around the first pair of magnets 202a, 202c defines a South pole A, the second wire 212 coiled around the second pair of magnets 202b, 202d defines a North pole C, and the third wire 214 coiled around the pair of neutral magnets 206a, 206b defines a neutral pole B. As will be appreciated by a person skilled in the art, when current is delivered to the first and second wires 210, 212, an electromagnetic field (the first electromagnetic field) is generated. The first plurality of magnets 202a, 202b, 202c, 202d alternately have north and south poles facing radially inward. Each of the first plurality of magnets 202a, 202b, 202c, 202d is a permanent magnet so as to always have north facing radially inward for the first pair of outer magnets 202a, 202c and south facing radially inward for the second pair of outer magnets 202b, 202d.

The second plurality of magnets 204a, 204b, 204c, 204d are located within an effective distance of the first plurality of magnets 202a, 202b, 202c, 202d such that the first electromagnetic field is configured to cause movement of the second plurality of magnets 204a, 204b, 204c, 204d. In particular, the second plurality of magnets 204a, 204b, 204c, 204d are configured to rotate as a unit, as shown by arrow R in FIG. 9, with a direction of the second plurality of magnets' rotation depending on the voltage input (positive or negative) to the first pair of permanent magnets 202a, 202c and the second pair of permanent magnets 202b, 202d, as will be appreciated by a person skilled in the art. The shaft 208 is operably coupled to the second plurality of magnets 204a, 204b, 204c, 204d and is configured to move with the second plurality of magnets 204a, 204b, 204c, 204d. The rotation of the second plurality of magnets 204a, 204b, 204c, 204d is thus configured to cause the shaft 208 to rotate in the same direction as the second plurality of magnets 204a, 204b, 204c, 204d. The rotation of the shaft 208 generates the torque delivered to the surgical tool coupled to the robotic surgical system that includes the motor 200.

A fourth wire 216 is coiled around a first pair of the second plurality of magnets 204a, 204c, and a fifth wire 218 is coiled around a second pair of the second plurality of magnets 204b, 204d. As shown in FIGS. 9 and 10, the fourth wire 216 coiled around the first pair of inner magnets 204a, 204c defines a pole D, and the fifth wire 218 coiled around the second pair of inner magnets 204b, 204d defines a pole E. As will be appreciated by a person skilled in the art, when current is delivered to the fourth and fifth wires 216, 218, an electromagnetic field (the second electromagnetic field) is generated. The second plurality of magnets 204a, 204b, 204c, 204d are located within an effective distance of the first plurality of magnets 202a, 202b, 202c, 202d, as mentioned above, which not only allows the first electromagnetic field to be in effective distance of the second plurality of magnets 204a, 204b, 204c, 204d but also allows the second electromagnetic field to be in effective distance of the first electromagnetic field. In other words, the second electromagnetic field can interfere with the first electromagnetic field.

Figure 11:
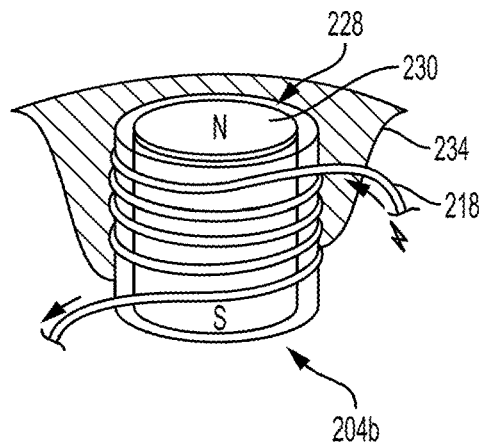
FIG. 11 is a perspective view of a portion of the motor of FIG. 9.

The second plurality of magnets 204a, 204b, 204c, 204d can have a variety of configurations. In general, each of the second plurality of magnets 204a, 204b, 204c, 204d can include a rare earth magnet and an iron member operatively coupled to the rare earth magnet. As in this illustrated embodiment of FIG. 10, each of the second plurality of magnets 204a, 204b, 204c, 204d can include a rare earth magnet and an iron member in the form of an iron sleeve that is disposed around the rare earth magnet. FIG. 11 illustrates one of the second plurality of magnets 204b showing its iron sleeve 228 disposed around the rare earth magnet 230 operatively coupled thereto, with the fifth wire 218 coiled around the iron sleeve 228 that surrounds the rare earth magnet 230 core of the magnet 204b. Each of the other second plurality of magnets 204a, 204c, 204d can similarly include an iron sleeve and rare earth magnet. FIGS. 9 and 11 also illustrate epoxy 234 disposed radially inward of the first plurality of magnets 202a, 202b, 202c, 202d.

In at least some embodiments, power for rare earth magnet core 230 dampening can be supplied by harvesting it from the rotation of the shaft 208 attached thereto, which may further dampen the torque capability of the motor 200.

Figure 12:
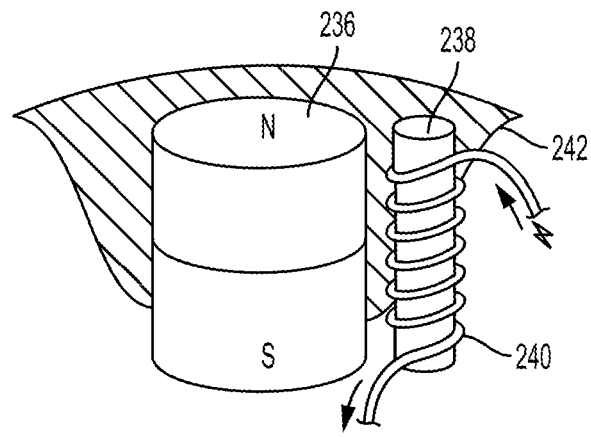
FIG. 12 is a perspective view of a portion of another embodiment of a motor.
Figure 13:
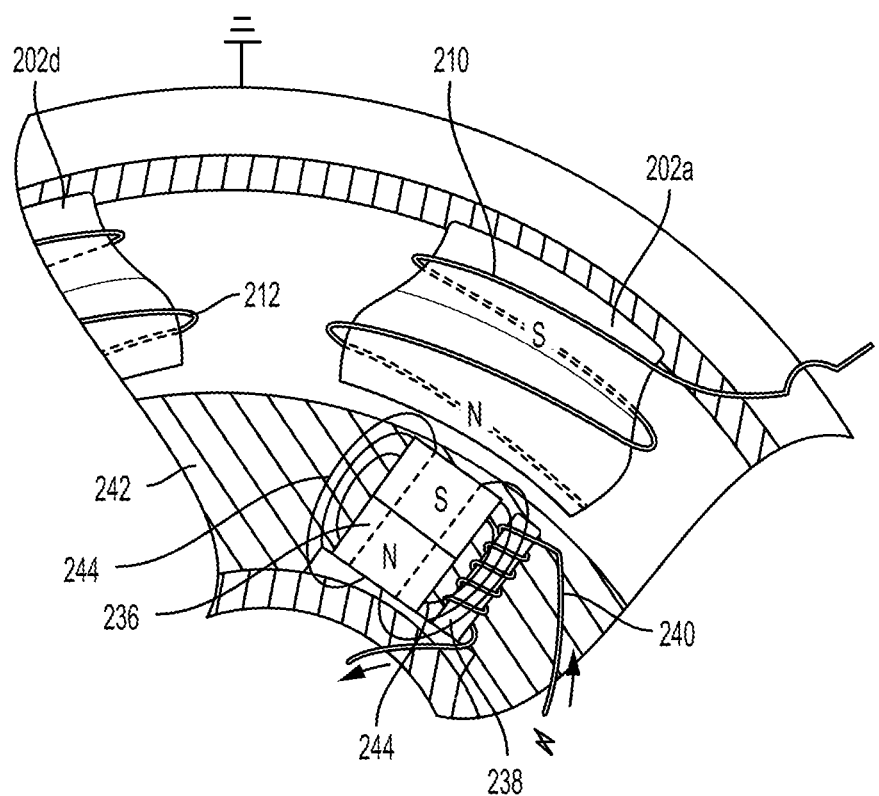
FIG. 13 is perspective view of an expanded portion of the motor of FIG. 12.

In another embodiment, shown in FIGS. 12 and 13, each of the motor's second plurality of magnets can include a rare earth magnet 236 separate from and in operative distance of an iron member in the form of an iron bar 238. The iron bar 238 has a wire 240 coiled therearound to which current is delivered for activation of the second electromagnetic field 244, which is partially shown in FIG. 14. By placing the iron member 238 near the rare earth magnet 236 but not around it, like the iron sleeve 228 that is disposed around the rare earth magnet 230 of FIG. 11, the iron member 238 (and wire 240 wrapped around it) can be within the second electromagnetic field 244 to more effectively dampen or reinforce than when the iron member is only partially or not within the second electromagnetic field as in, for example, the embodiment of FIG. 11. FIGS. 12 and 13 also illustrate epoxy 242 disposed radially inward of the first plurality of magnets 202a, 202b, 202c, 202d.

Figure 14:
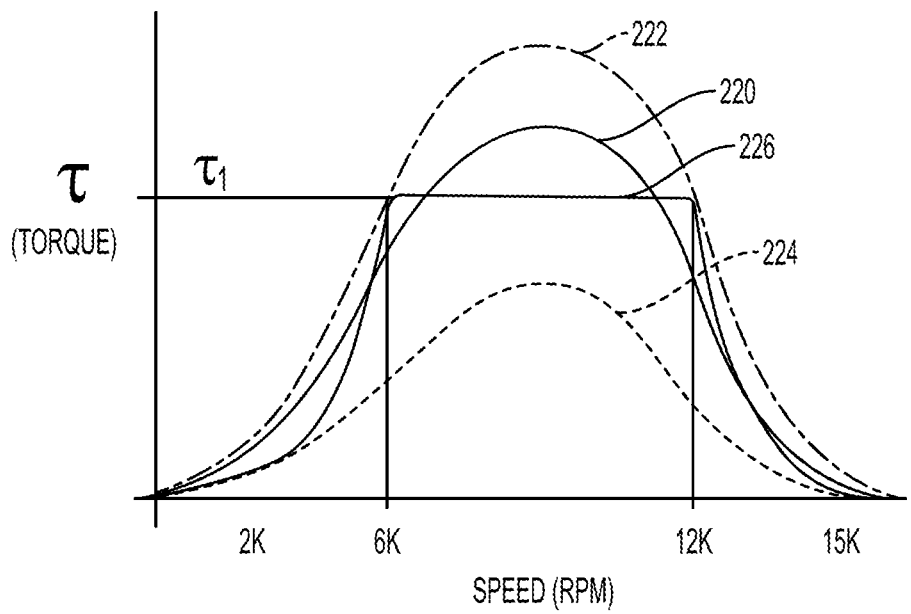
FIG. 14 is a graph showing torque versus speed for the motor of FIG. 9.

FIG. 14 illustrates a profile curve of the motor 200. Values of the speed of the motor 200 on the x axis are illustrative only, as other speeds are possible. In general, the profile curve shows that the motor 200 is configured to be electrically shiftable between a first predictable speed (a non-zero value, 6,000 rpm in this illustrated embodiment) and a second, greater predictable speed (12,000 rpm in this illustrated embodiment) by changing the second electromagnetic field, which can be accomplished by changing the voltage input to the motor 200. The first predictable speed is about twice that of the second predictable speed. A person skilled in the art will appreciate that a value may not be at a certain value, e.g., one speed may not be precisely double another speed, but nevertheless considered to be at about that certain value due to one or more factors, such as manufacturing tolerance and sensitivity of measuring equipment. The motor 200 can thus be configured to provide one of two predetermined speeds, which may allow for better user control of end effector function, allow for dynamic braking of end effector function (such as for better control of lockout at the end of an end effector function), and/or improve torque predictability. The shaft 208 of the motor 200 typically has a relatively small diameter to help reduce a size of the motor 200 and for the motor 200 to be desirable to use in a surgical setting. Mechanically shifting a motor used in a robotic surgical system may be difficult because of this small diameter and/or the limited amount of space in the device to accommodate mechanical parts needed to effect shifting. The motor 200 being electrically shiftable allows shifting without moving mechanical parts to effect the shifting and/or without the shaft's small size being problematic since shifting can be accomplished merely by modifying an electrical input to the motor 200.

The profile curve shows a normal curve 220 reflecting the first electromagnetic field being active (e.g., current is being delivered to the first and second wires 210, 212) without the second electromagnetic field being active (e.g., current is not being delivered to the fourth and fifth wires 216, 218). The normal curve 220 has a Gaussian or bell curve shape. The profile curve also shows a reinforced curve 222 reflecting the second electromagnetic field reinforcing, or strengthening, the first electromagnetic field and shows a dampened curve 224 reflecting the second electromagnetic field dampening, or weakening, the first electromagnetic field. Each of the reinforced and dampened curves 222, 224 has a Gaussian or bell curve shape. A resulting torque speed curve 226 of the normal, reinforced, and dampened curves 220, 222, 224 does not have a Gaussian or bell curve shape. Instead, the resulting torque speed curve 226 has a flattened aspect at torque Ti that extends between the first predictable speed and the second predictable speed. In other words, the torque of the motor 200 is substantially constant at speeds between the first and second predictable speeds. A person skilled in the art will appreciate that a value may not be at a certain value, e.g., the torque may not be precisely Ti in the flattened aspect of the curve 226, but nevertheless considered to be substantially at that certain value due to one or more factors, such as manufacturing tolerance and sensitivity of measuring equipment. The resulting torque speed curve 226 has a curved shape below the first predictable speed and a curved shape above the second predictable speed.

Figure 15:
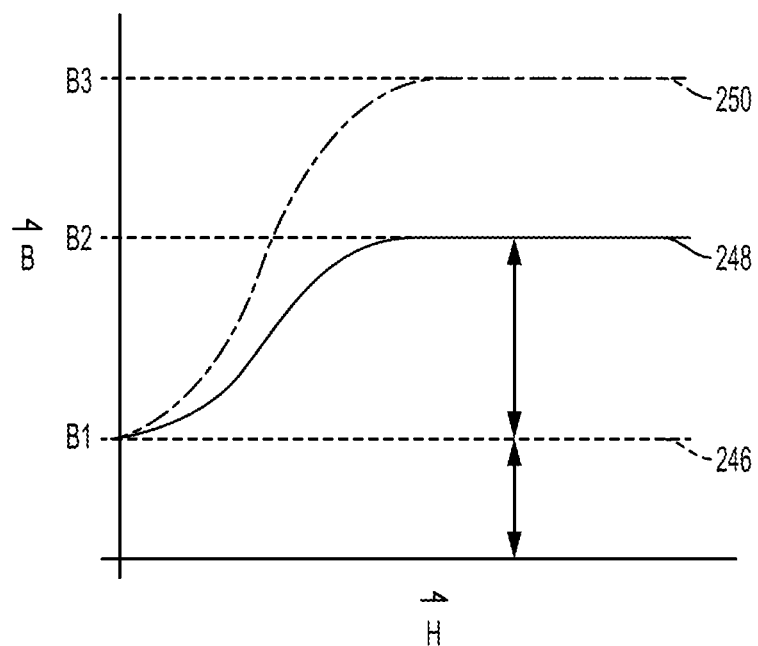
FIG. 15 is a graph illustrating an effect of the motor of FIG. 9.

FIG. 15 illustrates an effect of the reinforcement/dampening of FIG. 14. An inherent magnetic flux density B from the rare earth magnet of the second plurality of magnets 204a, 204b, 204c, 204d is shown by line 246 at B1. The inherent magnetic flux density B is substantially constant at B1 along values of magnetic field strength H. The magnetic flux density B from the iron member of the second plurality of magnets 204a, 204b, 204c, 204d is shown in an iron member curve 250. The iron member curve 250 curves upwards from B1 as magnetic field strength H until substantially leveling off at B3, which is greater than B1. The resulting electromagnetic field curve 248 curves upwards from B1 as magnetic field strength H until substantially leveling off at B2, which is greater than B1 and less than B3. The iron member thus helps increase the magnetic flux density B than can be provided by the rare earth magnet alone. The effect of the reinforcement/dampening using the iron member/rare earth magnet embodiment of FIG. 12 is similar to that of the effect in FIG. 15 for the iron member/rare earth magnet embodiment of FIG. 9 except that the iron member curve 250 may substantially level at a higher magnetic potential B.

In at least some embodiments, instead of having one wire wound around each of the motor's second plurality of magnets, a plurality of wires can be wound around each of the second plurality of magnets, which may allow for any shaped motor curve, not just those shown in FIG. 15.

Figure 16:
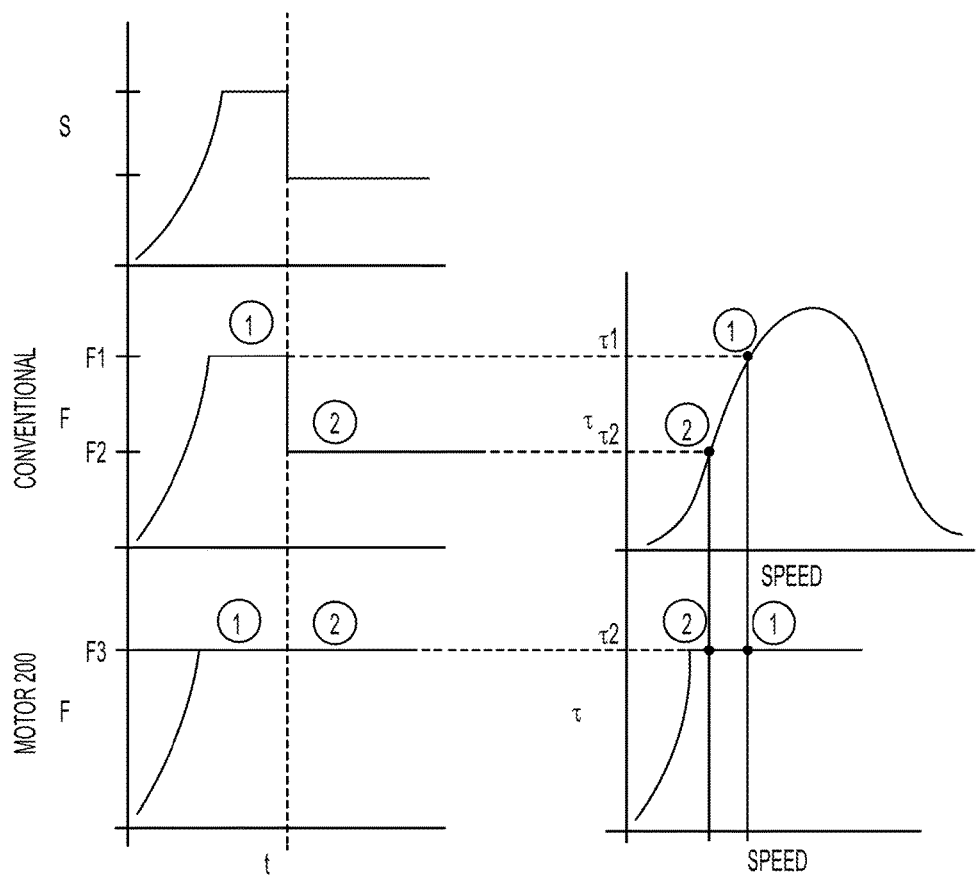
FIG. 16 are graphs showing profile curves of the motor of FIG. 9 and profile curves of a conventional motor.

FIG. 16 illustrates profile curves of the motor 200 as compared to profile curves for a conventional motor, e.g., a motor that does not have a second electromagnetic field. For the conventional motor, a first force F1 over a first time period corresponds to a first torque $\tau 1$ along a Gaussian or bell curve, and a second, lower force F2 over a second time period that is after the first time period corresponds to a first torque $\tau 1$ along the Gaussian or bell curve. In contrast, for the motor 200, a force F3 over the first and second time periods corresponds to a third torque $\tau 3$. The motor 200 can provide a substantially constant torque (e.g., the third torque $\tau 3$) over time and as motor speed increases, unlike the conventional motor. The motor 200 can maintain application of force F3, through maintaining the third torque $\tau 3$, which may facilitate end effector functions such as firing.

In at least some embodiments, torque provided by a robotic surgical system (e.g., a motor thereof) to a surgical tool releasably and replaceably coupled to the robotic surgical system can be configured to be prevented from exceeding a maximum predetermined amount of torque. Different surgical tools coupled to the robotic surgical system may be able to handle different maximum amounts of torque, so the motor of the robotic surgical system should be able to deliver torque up to at least the highest one of these maximum amounts of torque for the different ones of the surgical tools. However, this highest maximum amount of torque, and lower amounts down to a particular tool's maximum amount of acceptable torque, would be too much for at least some of the surgical tools to handle. Limiting the maximum amount of torque that the motor may provide to a surgical tool may thus help make it less likely that the surgical tool is damaged from too much torque being received and over-loading element(s) of the tool (e.g., the tool's elongate shaft, the tool's end effector, etc.) and/or help a function of the surgical tool be more precisely controlled. For example, different surgical tools configured to couple to the robotic surgical system and be driven by the same motor thereof may have elongate shafts of different diameters. Smaller diameter shafts are generally able to handle less torque than elongate shafts having larger diameters and/or are less able to resist torque from the motor than larger-diameter shaft tools. Thus, limiting the amount of torque that the motor provides to the particular surgical tool being driven may help prevent the motor, which is powerful enough to provide torque to larger-diameter shaft tools, from over-loading smaller-diameter shaft tools.

A robotic surgical system may include software configured to help prevent a surgical tool coupled to thereto from receiving too much torque from a motor of the robotic surgical system, but in the event of a software processing error, such a corrective measure will be ineffective. Torque provided to a surgical tool from the robotic surgical system being prevented from exceeding a maximum amount in another way, in addition to or instead of the software corrective measure, may avoid a single point failure that would occur in the software only solution since providing too much torque to the surgical tool may stop functionality of the surgical tool entirely.

The torque provided to a surgical tool from a robotic surgical system can be electronically prevented from exceeding a maximum amount of torque. The electronic prevention can include sensing at least one of a current applied to by the robotic surgical system to the surgical tool coupled thereto and a rotation of an elongate shaft of the surgical tool coupled to the robotic surgical system. Based on the sensed data, a motor of the robotic surgical system can be prevented from providing more than the maximum amount of torque to the surgical tool.

Figure 17:
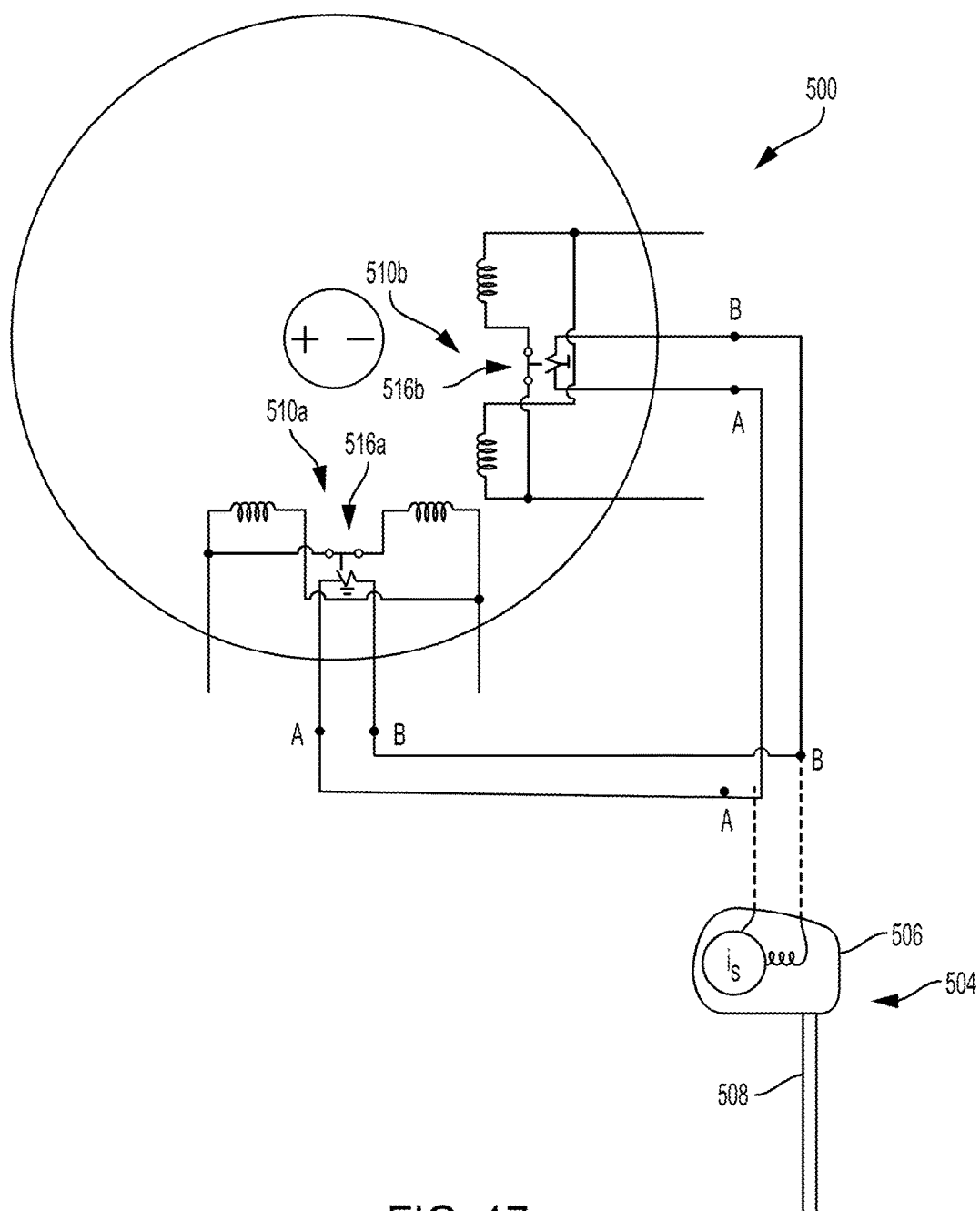
FIG. 17 is a schematic view of one embodiment of a system including a motor and a surgical tool coupled to the motor.
Figure 18:
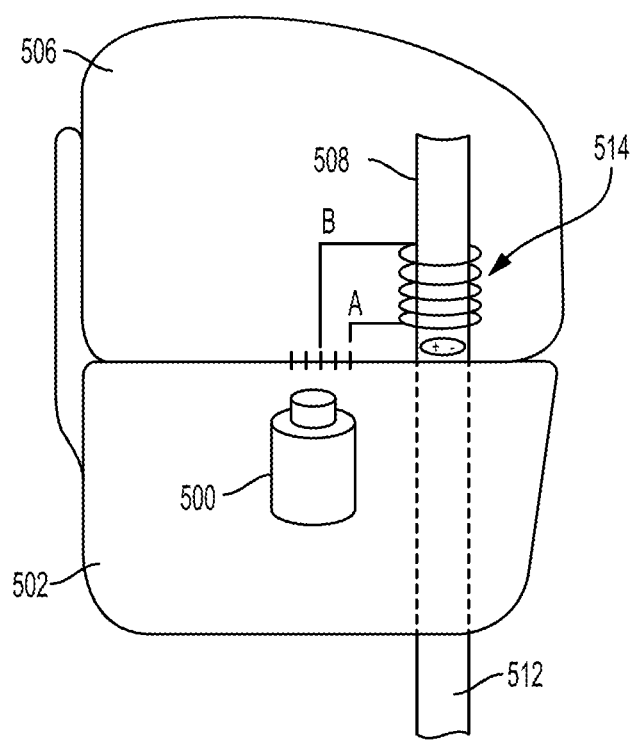
FIG. 18 is a side partially transparent schematic view of a proximal portion of the surgical tool of FIG. 17 coupled to a tool driver that includes the motor of FIG. 17.

FIGS. 17 and 18 illustrate one embodiment of a system in which torque provided by a motor 500 to a surgical tool 504 is prevented from exceeding a maximum amount of torque. The surgical tool 504 has a puck 506 coupled to a tool driver 502 that includes the motor 500, as shown in FIG. 18. As discussed herein, the tool driver 502 is a component of a robotic surgical system.

As shown in FIG. 17, the motor 500 includes a plurality of wire windings 510a, 510b configured to facilitate generation of an electromagnetic field in the motor 500. The electromagnetic field is configured to cause rotation of a shaft 512 operably coupled to an elongate shaft 508 of the surgical tool 504, as shown in FIG. 18. The motor 500 can be configured to only generate the one electromagnetic field or can be configured to generate a second electromagnetic field configured to interact with the electromagnetic field, as discussed herein. Examples of the wire windings 510a, 510b and associated electromagnetic field are the wire windings 210, 212 around magnets 202a, 202b, 202c, 202d of FIG. 9 configured to facilitate the generation of the first electromagnetic field. The motor 500 includes two wire windings 510a, 510b to generate the electromagnetic field, but a motor can have another number of wire windings, such as the motor 200 of FIG. 9 that has three wire windings 210, 212, 214.

Each of the motor's wire windings 510a, 510b has a switch 516a, 516b operatively coupled thereto. When the switches 516a, 516b are closed, their respective wire windings 510a, 510b allow current to flow therethrough to contribute to generation of the electromagnetic field. When the first switch 516a is open, the first wire winding 510a is open or interrupted such that the first wire winding 510a cannot contribute to generation of the electromagnetic field, e.g., only the second wire winding 510b contributes to generation of the electromagnetic field. Similarly, when the second switch 516b is open, the second wire winding 510b is open or interrupted such that the second wire winding 510b cannot contribute to generation of the electromagnetic field, e.g., only the first wire winding 510a contributes to generation of the electromagnetic field. The switches 510a, 510b are in the form of relay contact switches.

The puck 506 of the surgical tool 500 has the elongate shaft 508 extending distally therefrom and has an end effector (not shown) at a distal end of the elongate shaft 508. The elongate shaft 508 has a wire 514 wound therearound inside of the puck 506, as shown in FIG. 18. The wire 514 is configured to generate a current as the elongate shaft 508 rotates in response to torque delivered to the puck 506 from the tool driver 502, e.g., the rotation of the motor's shaft 512 drives the elongate shaft 508 to rotate. The wire 514 is operatively coupled to the switches 516a, 516b of the motor 500 as shown by couplings A and B in FIGS. 17 and 18. The current generated at the wire 514 is delivered to the motor 500, e.g., to the switches 516a, 516b, via the couplings A and B. When the delivered current exceeds a predetermined threshold for the first switch 516a, the current causes the first switch 516a to open, thereby preventing the first wire winding 510a from contributing to generation of the electromagnetic field and accordingly weakening the motor 500 and reducing an amount of the torque being delivered by the motor 500 to the surgical tool 504. Similarly, when the delivered current exceeds a predetermined threshold for the second switch 516b, the current causes the second switch 516b to open, thereby preventing the second wire winding 510b from contributing to generation of the electromagnetic field and accordingly weakening the motor 500 and reducing an amount of the torque being delivered by the motor 500 to the surgical tool 504. The switches 516a, 516b can be configured to trip open in response to the current from the tool 504 in any of a variety of ways, as will be appreciated by a person skilled in the art. A number of times that the wire 514 is wound around the shaft 508 can define the threshold amount of current that causes switch opening.

The current generated at the surgical tool 504 determines whether torque provided to the tool 504 is limited or not. The surgical tool 504 can thus be configured to limit a maximum torque delivered from the robotic surgical system the surgical tool 504, e.g., from the tool driver 502 to the puck 506. The surgical tool 504, e.g., the puck 506 thereof, can be configured to accomplish this by selectively disabling and enabling the windings 510a, 510b of the motor 500, as discussed above.

Figure 19:
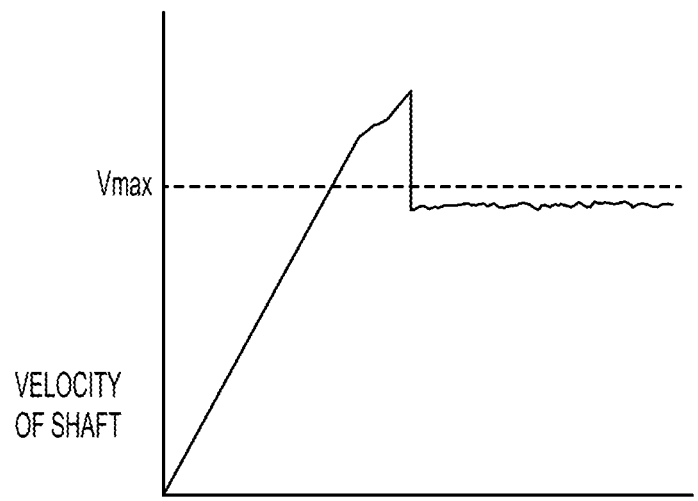
FIG. 19 is a graph showing operation of the motor of FIG. 17.

In general, the faster that the elongate shaft 508 is rotating, the more current is generated at the wire 514. Velocity of the elongate shaft 508 is thus proportionally related to the current. FIG. 19 illustrates a graph illustrating the opening of one of the switches 516a, 516b in response to a velocity of the elongate shaft 508 exceeding a predetermined threshold amount of velocity Vmax, after which the velocity decreases to be below the predetermined threshold amount of velocity Vmax.

Although each of the windings 510a, 510b has an associated switch 516a, 516b, in other embodiments, only one of the windings 510a, 510b may have an associated switch. In such an embodiment, the one of the windings without an associated switch will always be available to contribute to generation of the electromagnetic field while the other one of the windings will be selectively available to contribute to generation of the electromagnetic field based on the current delivered to the motor from the surgical tool.

Figure 20:
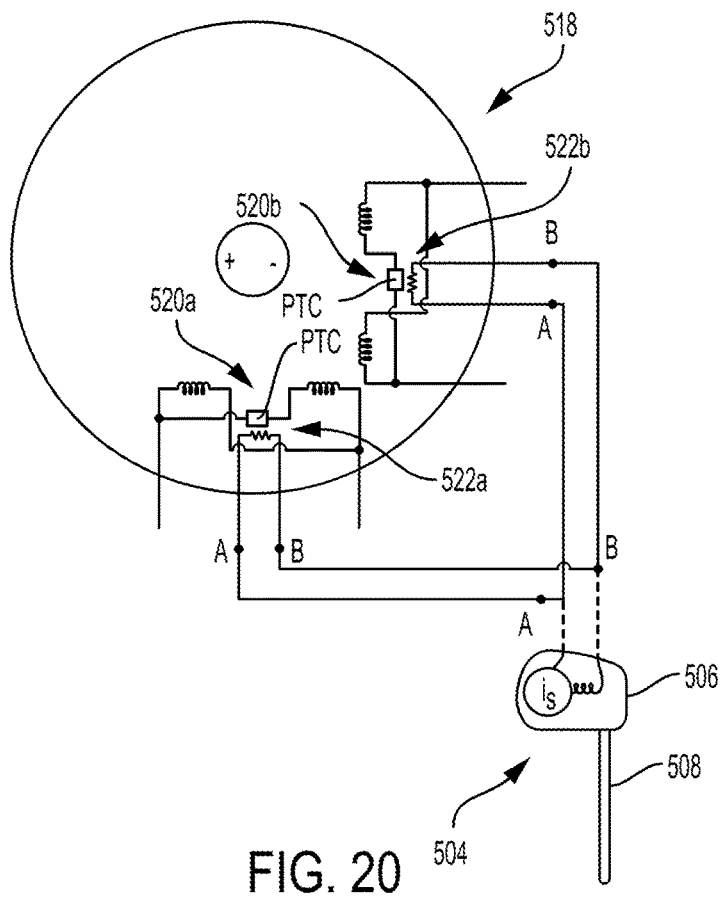
FIG. 20 is a schematic view of another embodiment of a system including a motor and a surgical tool coupled to the motor.

FIG. 20 illustrates another embodiment of a system in which torque provided by a motor 518 to the surgical tool 504 is prevented from exceeding a maximum amount of torque. The surgical tool 504 is the same tool as in FIGS. 17 and 18. The motor 518 is similar to the motor of FIGS. 17 and 18 except that its 520a, 520b are shown as positive temperature coefficient (PTC) switches thermally coupled to associated resistors 522a, 522b. When the current received from the surgical tool 504 is sufficient to raise the temperatures of the resistor 522a, 522b beyond their respective limits, the PTC element 520a, 520b associated with the resistor 522a, 522b having the limit-exceeding temperature will be tripped. Power is not interrupted by tripping of a PTC switch as with the relay contact switches 510a, 510b of FIG.

17. Instead, the tripping of a PTC switch denies current flow. The graph of FIG. 19 also illustrates the functionality of the embodiment of FIG. 20.

In another embodiment, instead of a tool driver (e.g., a motor thereof) including PTC switches like in the embodiment of FIG. 20, a surgical tool configured to couple to the tool driver can include a PTC switch. When current generated at a wire coiled around an elongate shaft of the tool exceeds a predetermined limit, the PTC switch can be tripped and deny current flow to the motor of the tool driver, similar to that discussed above. The PTC switch can be accessible through an electrical contact between the surgical tool (e.g., a puck thereof) and the tool driver, which may allow the surgical tool to apply a physical limit to the torque from the motor.

In the embodiments of FIGS. 17-20, an output (e.g., output current) of the surgical tool 504 is configured to control torque output of the motor operatively coupled thereto. In other embodiments, a motor can be configured to self-regulate its torque output to a surgical tool operatively coupled thereto.

Figure 21:
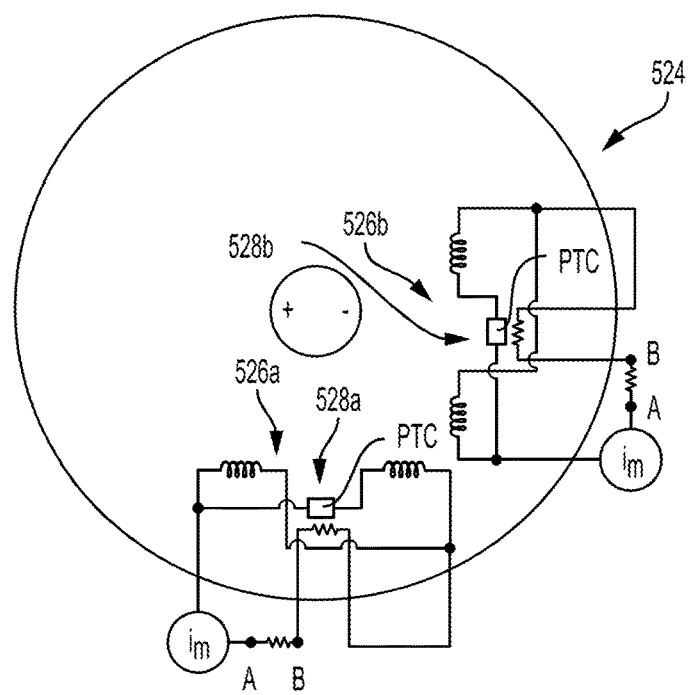
FIG. 21 is a schematic view of another embodiment of a motor.

FIG. 21 illustrates one embodiment of a system in which torque provided by a motor 524 to a surgical tool, such as the surgical tool 430 of FIG. 4, is prevented by the motor 524 from exceeding a maximum amount of torque based. The motor 524 is similar to the motor 518 of FIG. 20 in that its wire windings 526a, 526b are each operatively coupled to a PTC switch 528a, 528b. However, instead of the PTC switches 528a, 528b being configured to open in response to current received from the surgical tool to which the tool driver including the motor 524 is coupled, the PTC switches 528a, 528b being configured to open in response to the current in the respective ones of their wire windings 526a, 526b. In other words, the switches 528a, 528b receive current via couplings A and B at the motor 524 instead of via couplings A and B at the surgical tool as in the embodiments of FIGS. 17-20.

Figure 22:
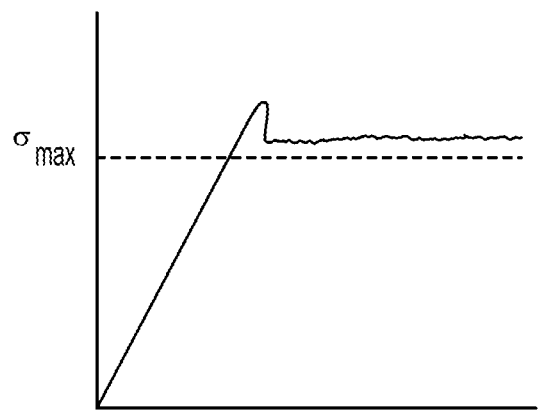
FIG. 22 is a graph showing operation of the motor of FIG. 21.

In general, the faster that a shaft of the motor 524 is rotating, the more current is at the wire windings 526a, 526b. FIG. 22 illustrates a graph illustrating the opening of one of the switches 528a, 528b in response to electrical conductivity exceeding a predetermined threshold amount of electrical conductivity σmax, after which the electrical conductivity decreases to approach the predetermined threshold amount of electrical conductivity σmax. Such functionality can be used for a variety of surgical tool functions, such as firing, e.g., adaptive firing.

In the embodiments of FIGS. 17-22, motor control is configured to occur dynamically during use of the motor. In other embodiments, a motor can be configured to be controlled to have its torque limited in response to a surgical tool being operably coupled thereto before the motor begins providing any torque to the surgical tool or at substantially a same time that the motor first begins providing the torque to the surgical tool.

Figures 23, 24:
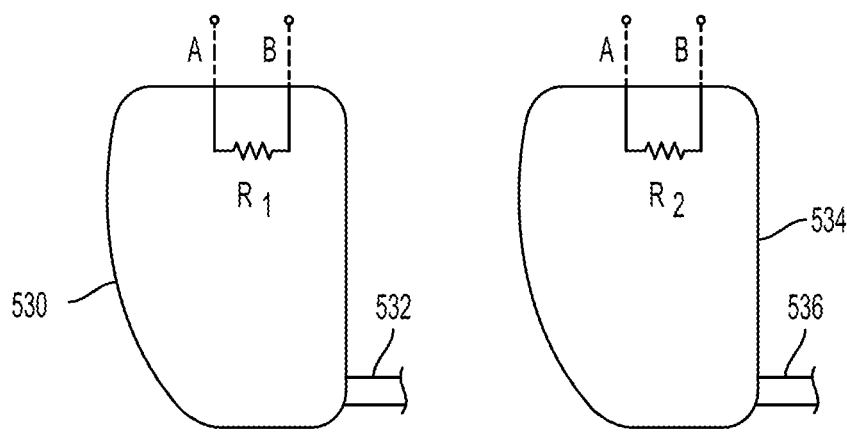
FIG. 23 is a side partially transparent schematic view of a proximal portion of one embodiment of a surgical tool.
FIG. 24 is a side partially transparent schematic view of a proximal portion of another embodiment of a surgical tool.
Figure 25:
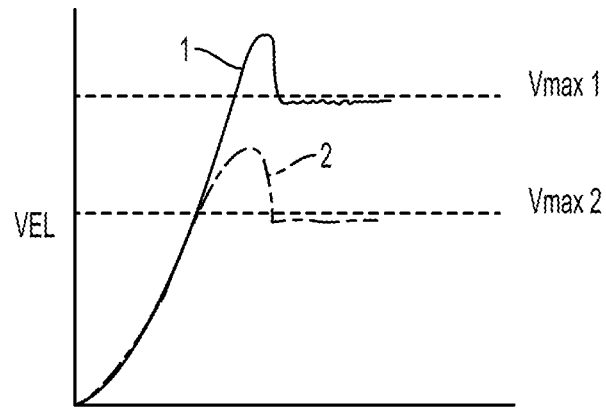
FIG. 25 is a graph showing operation of a motor coupled to the surgical tools of FIGS. 23 and 24.

FIG. 24 illustrates one embodiment of a puck 530 configured to control a torque output of a motor and having an elongate shaft 532 extending distally from the puck 530. The puck 530 includes a resistor R1 disposed therein that is configured to operably couple to windings of the motor via couplings A and B. The resistor R1 is configured to pre-set a speed limit of the motor. FIG. 25 illustrates another embodiment of a puck 534 configured to control a torque output of a motor and having an elongate shaft 536 extending distally from the puck 534. The puck 536 includes a resistor R2 disposed therein that is configured to operably couple to windings of the motor via couplings A and B. The resistor R2 is configured to pre-set a speed limit of the motor. As shown in FIG. 25, the resistor R2 of FIG. 25 is configured to allow a weaker maximum velocity Vmax2 of the motor than the resistor R1 of FIG. 24, which is configured to allow a stronger maximum velocity Vmax1 of the motor. Thus, choosing a size of the resistor in the puck may allow different maximum motor velocities to be set for different surgical tools. In general, the larger the resistor, the less the resistor will disable the motor's torque output.

Figure 27:
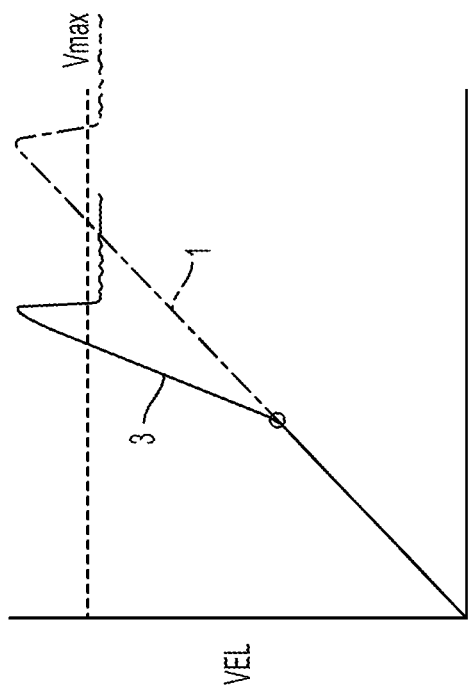
FIG. 27 is a graph showing operation of a motor coupled to the surgical tools of FIGS. 23 and 26.
Figure 26:
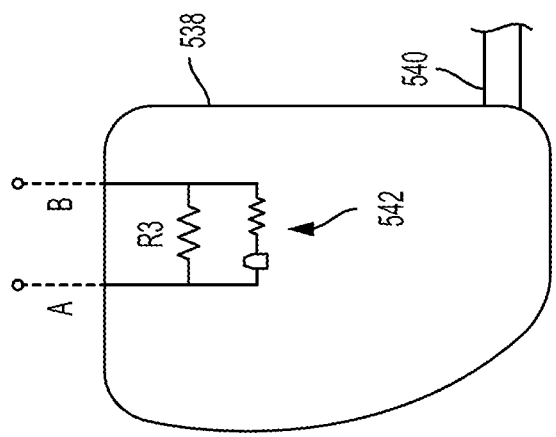
FIG. 26 is a side partially transparent schematic view of a proximal portion of another embodiment of a surgical tool.

FIG. 26 illustrates another embodiment of a puck 538 configured to control a torque output of a motor and having an elongate shaft 540 extending distally from the puck 538. The puck 538 includes a PTC switch, including a resistor R3 and a PTC element 542, disposed therein that is configured to operably couple to windings of the motor via couplings A and B. The PTC switch is configured to cooperate to pre-set a speed limit of the motor. As shown in FIG. 27, the resistor PTC switch of FIG. 26 is configured to more quickly adjust the motor's maximum velocity to be below maximum velocity Vmax than the resistor R1 of FIG. 24.

Figure 28:
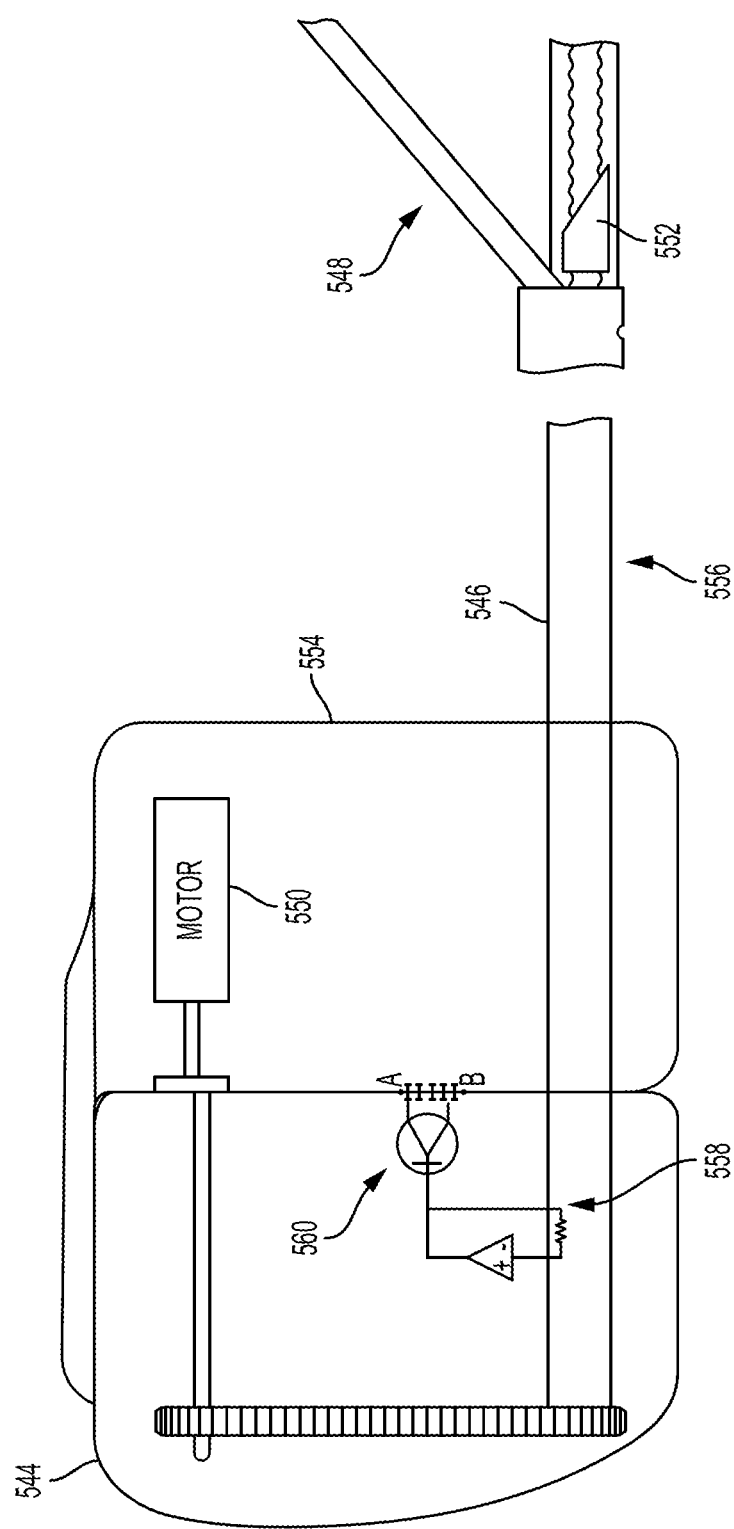
FIG. 28 is a side partially transparent view of portions of another embodiment of a surgical tool coupled to a tool driver.
Figure 28A:
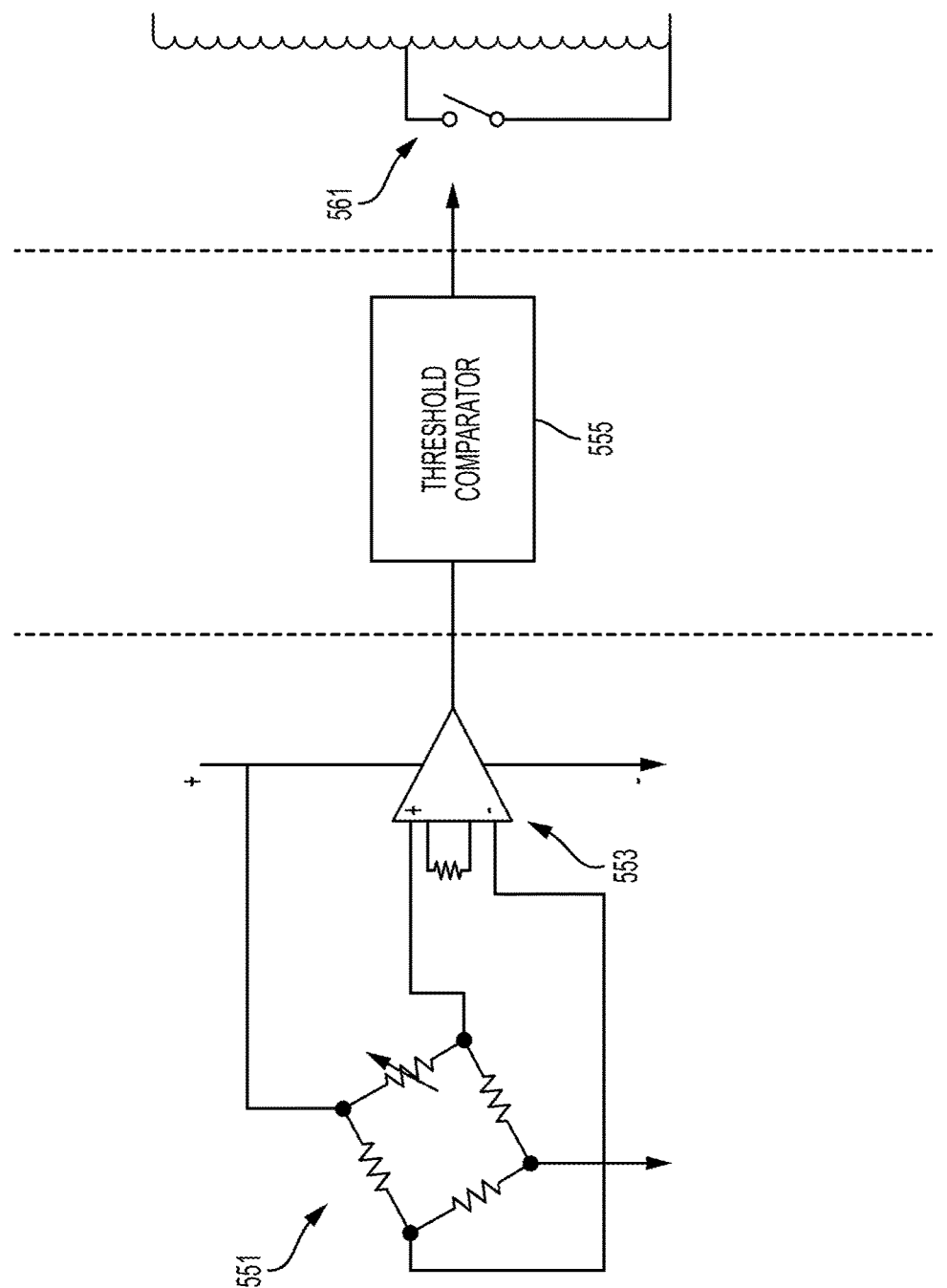
FIG. 28A is a schematic view of an alternate embodiment of the surgical tool of FIG. 28.

FIG. 28 illustrates another embodiment of a puck 544 configured to control a torque output of a motor 550 of a tool driver 554 coupled to a surgical tool 556 that includes the puck 544. FIG. 28 also shows an elongate shaft 546 extending distally from the puck 544 and an end effector 548 at a distal end of the elongate shaft 546 and a knife 552 configured to translate along the end effector 548. The puck 544 includes a strain gauge 558. Distal pushing motion at the surgical tool 556 driven by the motor 550 will have channel resistance, such as when the knife 552 is pushed distally along the end effector 548. The strain gauge 558 can be operatively coupled to any element in the puck 544 that may experience a high load, such as at a channel retainer, a firing rod, etc., from distal pushing motion. The strain gauge 558 is configured to measure the channel resistance, e.g., the force that the element coupled to the strain gauge 558 is resisting in response to the distal force applied to the end effector, and communicate the measured channel resistance to an amplifier 560 disposed in the puck 544. The amplifier 560 is configured to amplify the measured channel resistance and deliver it to the motor 550 via couplings A and B to selectively turn on or off wire windings of the motor 550, similar to that discussed above regarding current delivery enabling or disabling a motor's wire windings. For example, distal pushing force above 20 lb may be undesirable due to mechanical constraints of the surgical tool 556, and the puck 544 can be configured to prevent force from being applied that would exceed a 20 lb maximum limit. FIG. 28A illustrates a portion of an alternate embodiment of the puck 544. In this setup, a strain gauge 551, amplifier 553 (e.g., an AD822 amplifier available from Analog Devices, Inc. of Norwood, Mass.), and threshold detector 555 are configured to measure the channel resistance, e.g., the force that the element coupled to the strain gauge 551, amplifier 553 and threshold detector 555 is resisting in response to the distal force applied to the end effector, and when the strain measured by the strain gauge 551, amplifier 553, and threshold detector 588 exceeds a pre-determined threshold, a switch 561 disposed in the puck 544 is activated. The switch 561 is connected to the motor 550 via couplings A and B to selectively turn on or off wire windings of the motor 550, similar to that discussed above regarding current delivery enabling or disabling a motor's wire windings.

Terminology

Figure 29:
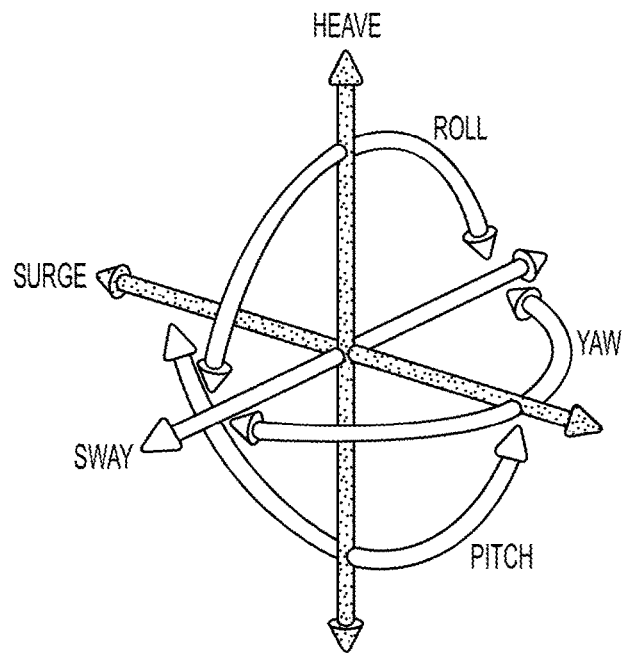
FIG. 29 is a graphical representation of terminology associated with six degrees of freedom.

There are a number of ways in which to describe the movement of a surgical system, as well as its position and orientation in space. One particularly convenient convention is to characterize a system in terms of its degrees of freedom. The degrees of freedom of a system are the number of independent variables that uniquely identify its pose or configuration. The set of Cartesian degrees of freedom is usually represented by the three translational or position variables, e.g., surge, heave, and sway, and by the three rotational or orientation variables, e.g., Euler angles or roll, pitch, and yaw, that describe the position and orientation of a component of a surgical system with respect to a given reference Cartesian frame. As used herein, and as illustrated in FIG. 29, the term "surge" refers to forward and backward movement, the term "heave" refers to movement up and down, and the term "sway" refers to movement left and right. With regard to the rotational terms, "roll" refers to tilting side to side, "pitch" refers to tilting forward and backward, and "yaw" refers to turning left and right. In a more general sense, each of the translation terms refers to movement along one of the three axes in a Cartesian frame, and each of the rotational terms refers to rotation about one of the three axes in a Cartesian frame.

Although the number of degrees of freedom is at most six, a condition in which all the translational and orientation variables are independently controlled, the number of joint degrees of freedom is generally the result of design choices that involve considerations of the complexity of the mechanism and the task specifications. For non-redundant kinematic chains, the number of independently controlled joints is equal to the degree of mobility for an end effector. For redundant kinematic chains, the end effector will have an equal number of degrees of freedom in Cartesian space that will correspond to a combination of translational and rotational motions. Accordingly, the number of degrees of freedom can be more than, equal to, or less than six.

With regard to characterizing the position of various components of the surgical system and the mechanical frame, the terms "forward" and "rearward" may be used. In general, the term "forward" refers to an end of the surgical system that is closest to the distal end of the input tool, and when in use in a surgical procedure, to the end disposed within a patient's body. The term "rearward" refers to an end of the surgical system farthest from the distal end of the input tool, and when in use, generally to the end farther from the patient.

The terminology used herein is not intended to limit the invention. For example, spatially relative terms, e.g., "superior," "inferior," "beneath," "below," "lower," "above," "upper," "rearward," "forward," etc., may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "inferior to" or "below" other elements or features would then be "superior to" or "above" the other elements or features. Likewise, descriptions of movement along and around various axes include various special device positions and orientations. As will be appreciated by those skilled in the art, specification of the presence of stated features, steps, operations, elements, and/or components does not preclude the presence or addition of one or more other features, steps, operations, elements, components, and/or groups described herein. In addition, components described as coupled may be directly coupled, or they may be indirectly coupled via one or more intermediate components.

There are several general aspects that apply to the various descriptions below. For example, at least one surgical end effector is shown and described in various figures. An end effector is the part of a surgical instrument or assembly that performs a specific surgical function, e.g., forceps/graspers, needle drivers, scissors, electrocautery hooks, staplers, clip appliers/removers, suction tools, irrigation tools, etc. Any end effector can be utilized with the surgical systems described herein. Further, in exemplary embodiments, an end effector can be configured to be manipulated by a user input tool. The input tool can be any tool that allows successful manipulation of the end effector, whether it be a tool similar in shape and style to the end effector, such as an input tool of scissors similar to end effector scissors, or a tool that is different in shape and style to the end effector, such as an input tool of a glove dissimilar to end effector graspers, and such as an input tool of a joystick dissimilar to end effector graspers. In some embodiments, the input tool can be a larger scaled version of the end effector to facilitate ease of use. Such a larger scale input tool can have finger loops or grips of a size suitable for a user to hold. However, the end effector and the input tool can have any relative size.

A slave tool, e.g., a surgical instrument, of the surgical system can be positioned inside a patient's body cavity through an access point in a tissue surface for minimally invasive surgical procedures. Typically, cannulas such as trocars are used to provide a pathway through a tissue surface and/or to prevent a surgical instrument or guide tube from rubbing on patient tissue. Cannulas can be used for both incisions and natural orifices. Some surgical procedures require insufflation, and the cannula can include one or more seals to prevent excess insufflation gas leakage past the instrument or guide tube. In some embodiments, the cannula can have a housing coupled thereto with two or more sealed ports for receiving various types of instruments besides the slave assembly. As will be appreciated by a person skilled in the art, any of the surgical system components disclosed herein can have a functional seal disposed thereon, therein, and/or therearound to prevent and/or reduce insufflation leakage while any portion of the surgical system is disposed through a surgical access port, such as a cannula. The surgical systems can also be used in open surgical procedures. As used herein, a surgical access point is a point at which the slave tool enters a body cavity through a tissue surface, whether through a cannula in a minimally invasive procedure or through an incision in an open procedure.

Computer Systems

The systems, devices, and methods disclosed herein can be implemented using one or more computer systems, which may also be referred to herein as digital data processing systems and programmable systems.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 30:
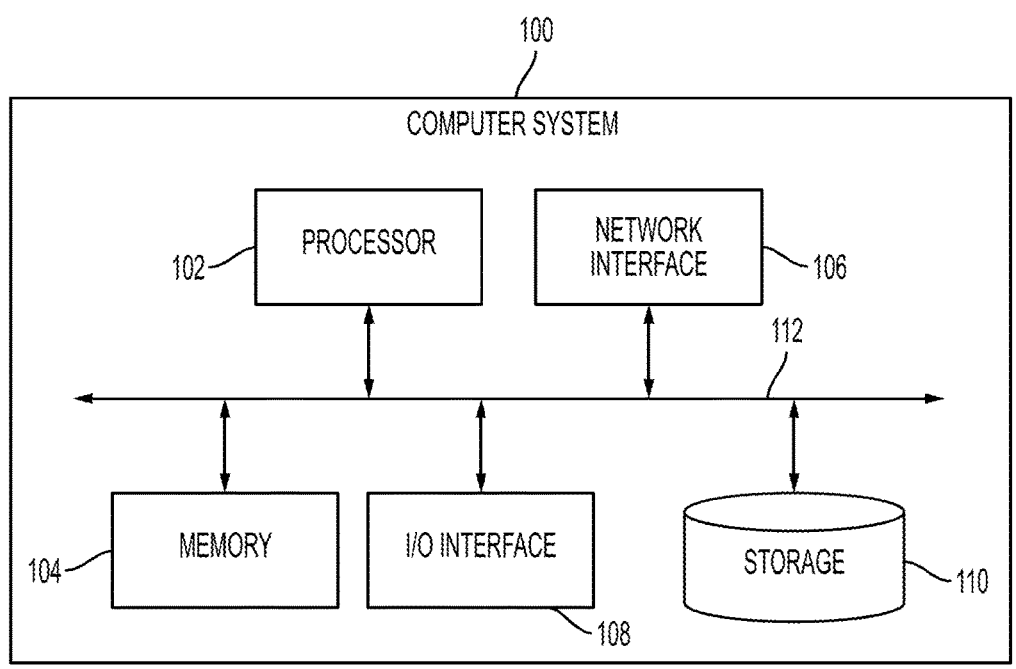
FIG. 30 is a schematic view of one embodiment of a computer system.

FIG. 30 illustrates one exemplary embodiment of a computer system 100. As shown, the computer system 100 includes one or more processors 102 which can control the operation of the computer system 100. "Processors" are also referred to herein as "controllers." The processor(s) 102 can include any type of microprocessor or central processing unit (CPU), including programmable general-purpose or special-purpose microprocessors and/or any one of a variety of proprietary or commercially available single or multi-processor systems. The computer system 100 can also include one or more memories 104, which can provide temporary storage for code to be executed by the processor(s) 102 or for data acquired from one or more users, storage devices, and/or databases. The memory 104 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 100 can be coupled to a bus system 112. The illustrated bus system 112 is an abstraction that represents any one or more separate physical busses, communication lines/interfaces, and/or multi-drop or point-to-point connections, connected by appropriate bridges, adapters, and/or controllers. The computer system 100 can also include one or more network interface(s) 106, one or more input/output (TO) interface(s) 108, and one or more storage device(s) 110.

The network interface(s) 106 can enable the computer system 100 to communicate with remote devices, e.g., other computer systems, over a network, and can be, for non-limiting example, remote desktop connection interfaces, Ethernet adapters, and/or other local area network (LAN) adapters. The IO interface(s) 108 can include one or more interface components to connect the computer system 100 with other electronic equipment. For non-limiting example, the IO interface(s) 108 can include high speed data ports, such as universal serial bus (USB) ports, 1394 ports, Wi-Fi, Bluetooth, etc. Additionally, the computer system 100 can be accessible to a human user, and thus the IO interface(s) 108 can include displays, speakers, keyboards, pointing devices, and/or various other video, audio, or alphanumeric interfaces. The storage device(s) 110 can include any conventional medium for storing data in a non-volatile and/or non-transient manner. The storage device(s) 110 can thus hold data and/or instructions in a persistent state, i.e., the value(s) are retained despite interruption of power to the computer system 100. The storage device(s) 110 can include one or more hard disk drives, flash drives, USB drives, optical drives, various media cards, diskettes, compact discs, and/or any combination thereof and can be directly connected to the computer system 100 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 30 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 100 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 100 can also include a web server for generating and/or delivering the web pages to client computer systems.

In an exemplary embodiment, the computer system 100 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Reuse

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical apparatus, comprising:
a motor of a robotic surgical system, the motor being configured to provide torque to a surgical tool removably and replaceably coupled to the robotic surgical system, and the motor including a first plurality of magnets configured to generate a first electromagnetic field and a second plurality of magnets configured to generate a second electromagnetic field, wherein the motor is configured to provide a first amount torque to the surgical tool and a second amount of torque to the surgical tool in response to interference of the second electromagnetic field with the first electromagnetic field.

2. The apparatus of claim 1, further comprising a tool driver of the robotic surgical system, the tool driver having the motor disposed therein, and the tool driver being configured to removably and replaceably couple to the surgical tool.

3. The apparatus of claim 1, wherein the provided torque drives a function of the surgical tool.

4. The apparatus of claim 1, wherein the first amount of torque is greater than the second amount of torque.

5. The apparatus of claim 1, wherein the first amount of torque is less than the second amount of torque.

6. The apparatus of claim 1, wherein the first plurality of magnets are arranged radially around the second plurality of magnets.

7. The apparatus of claim 1, wherein each of the second plurality of magnets includes an iron member and a rare earth magnet operatively coupled to the iron member.

8. The apparatus of claim 7, wherein each of the iron members is an iron sleeve disposed around the rare earth magnet operatively coupled thereto such that the motor includes a plurality of paired iron sleeves and rare earth magnets.

9. The apparatus of claim 7, wherein each of the iron members is an iron bar separate from and in operative distance of the rare earth magnet operatively coupled thereto.

10. The apparatus of claim 1, wherein the second plurality of magnets includes a first pair of magnets and a second pair of magnets, each pair having a wire coiled therearound.

11. A surgical method, comprising:
causing a motor of a robotic surgical system to generate a first electromagnetic field to provide a first amount of torque to a surgical tool removably and replaceably coupled to the robotic surgical system and thereby causing movement of the surgical tool; and
causing the motor to generate a second electromagnetic field to interfere with the first electromagnetic field such that the first amount of torque being provided to the surgical tool is adjusted to a second amount of torque.

12. The method of claim 11, wherein the first amount of torque provided to the surgical tool causes the surgical tool to perform one of open an end effector of the surgical tool, close the end effector, articulate the end effector relative to an elongate shaft of the surgical tool, rotate the end effector relative to the elongate shaft, and rotate the end effector and the elongate shaft as a unit about a longitudinal axis of the shaft; and
the second amount of torque provided to the surgical tool causes the surgical tool to perform a different one of open the end effector, close the end effector, articulate the end effector relative to an elongate shaft of the surgical tool, rotate the end effector relative to the elongate shaft, and rotate the end effector and the elongate shaft as a unit about a longitudinal axis of the shaft.

13. The method of claim 11, wherein the first amount of torque is greater than the second amount of torque.

14. The method of claim 11, wherein the first amount of torque is less than the second amount of torque.

15. The method of claim 11, further comprising varying a voltage input to the motor to dampen or strengthen the second electromagnetic field.

16. A surgical apparatus, comprising:
- a motor of a robotic surgical system, the motor being configured to generate a first electromagnetic field to provide a first amount of torque to a surgical tool removably and replaceably coupled to the robotic surgical system, and the motor being configured to generate a second electromagnetic field that is configured to interfere with the first electromagnetic field and thereby adjust the first amount of torque to a second amount of torque that is different than the first amount of torque.

17. The apparatus of claim 16, wherein the first amount of torque is greater than the second amount of torque.

18. The apparatus of claim 16, wherein the first amount of torque is less than the second amount of torque.

19. The apparatus of claim 16, further comprising a tool driver of the robotic surgical system, the tool driver having the motor disposed therein, and the tool driver being configured to removably and replaceably couple to the surgical tool.

20. The apparatus of claim 16, wherein the first and second amounts of torque each drive a function of the surgical tool removably and replaceably coupled to the robotic surgical system.

\* \* \* \* \*